(12) United States Patent
Kjeldsen et al.

(10) Patent No.: US 6,500,645 B1
(45) Date of Patent: Dec. 31, 2002

(54) N-TERMINALLY EXTENDED PROTEINS EXPRESSED IN YEAST

(75) Inventors: Thomas Børglum Kjeldsen, Virum (DK); Per Balschmidt, Espergærde (DK); Annette Frost Pettersson, Farum (DK); Knud Vad, Vanløse (DK); Jakob Brandt, Broenshoej (DK); Svend Havelund, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/324,217

(22) Filed: Jun. 2, 1999

Related U.S. Application Data

(63) Continuation-in-part of application No. 08/991,801, filed on Dec. 16, 1997, now abandoned, and a continuation-in-part of application No. 08/766,011, filed on Dec. 13, 1996, now abandoned, and a continuation-in-part of application No. 08/490,689, filed on Jun. 15, 1995, now abandoned, which is a continuation of application No. 08/286,059, filed on Aug. 4, 1994, now abandoned.

(30) Foreign Application Priority Data

Jun. 17, 1994 (DK) ................................. 0712/94
Dec. 20, 1995 (DK) ................................. 1449/95
Dec. 20, 1996 (DK) ................................. 1482/96

(51) Int. Cl.⁷ ............................. C12P 21/06; C12N 9/00
(52) U.S. Cl. ................. 435/69.7; 435/183; 435/254.11; 435/254.21; 435/320.1; 435/69.1; 435/69.8; 536/23.1; 536/23.2; 536/23.5; 536/23.51; 536/23.7; 536/23.74; 530/23.4
(58) Field of Search ............................. 435/69.7, 69.1, 435/69.8, 183, 254.11, 254.21, 320.1; 536/23.1, 23.2, 23.5, 23.4, 23.51, 23.7, 23.74

(56) References Cited

U.S. PATENT DOCUMENTS 4,546,082 A   10/1985   Kurjan et al. ............ 435/172.3

FOREIGN PATENT DOCUMENTS

| EP | 0 088 632 | 9/1983 |
| EP | 0 100 561 | 2/1984 |
| EP | 0 116 201 | 8/1984 |
| EP | 0 123 289 | 10/1984 |
| EP | 0 123 294 | 10/1984 |
| EP | 0 123 544 | 10/1984 |
| EP | 0 163 529 | 12/1985 |
| EP | 0 206 783 | 12/1986 |
| EP | 0 301 669 | 2/1989 |
| EP | 0 324 274 | 7/1989 |
| WO | WO 86/06406 | 11/1986 |
| WO | WO 90/10075 | 9/1990 |
| WO | WO 92/11378 | 7/1992 |
| WO | WO 92/13951 | 8/1992 |
| WO | WO 95/02059 | 1/1995 |
| WO | WO 95/34666 | 12/1995 |
| WO | WO 95/35384 | 12/1995 |

OTHER PUBLICATIONS

Roberds et al. Primary Structure and Muscle–specific Expression of the 50–kDa Dystrophin–associated Glycoprotein (Adhalin) Journal of Biological Chemistry 268 (32): 23739–23742, Nov. 1993.*
Julius et al. (1984) Cell 37:1075–1089.
Pfeffer et al. (1987) Ann. Rev. Biochem. 56:829–52.
Kurjan et al. (1982) Cell 30:933–943.
Egel–Mitani et al. (1990) 6:127–137.
Ohara et a. (1989) J. Biol. Chem. 264(34):20625–20631.

* cited by examiner

Primary Examiner—Rebecca E. Prouty
Assistant Examiner—Richard Hutson
(74) Attorney, Agent, or Firm—Reza Green, Esq.; Richard Bora

(57) ABSTRACT

The present invention relates to polypeptides expressed and processed in yeast, a DNA construct comprising a DNA sequence encoding such polypeptides, vectors carrying such DNA fragments and yeast cells transformed with the vectors, as well as a process of producing heterologous proteins in yeast.

35 Claims, 21 Drawing Sheets

```
                                                     EcoRI
    GTTTGTATTCTTTTCTTGCTTAAATCTATAACTACAAAAAACACATACAGGAATTCCATT
    ---------+---------+---------+---------+---------+---------+
 5  CAAACATAAGAAAAGAACGAATTTAGATATTGATGTTTTTTGTGTATGTCCTTAAGGTAA

CAAGAATAGTTCAAACAAGAAGATTACAAACTATCAATTTCATACACAATATAAACGATT
    ---------+---------+---------+---------+---------+---------+
    GTTCTTATCAAGTTTGTTCTTCTAATGTTTGATAGTTAAAGTATGTGTTATATTTGCTAA

AAAAGAATGAGATTTCCTTCAATTTTTACTGCAGTTTTATTCGCAGCATCCTCCGCATTA
10  ---------+---------+---------+---------+---------+---------+
    TTTTCTTACTCTAAAGGAAGTTAAAAATGACGTCAAAATAAGCGTCGTAGGAGGCGTAAT
         -MetArgPheProSerIlePheThrAlaValLeuPheAlaAlaSerSerAlaLeu
         <<<<<<<<<<<<<<<<<<<<<<<<<<<<<<<<<<<<<<<<<<<<<<<<<<<<<<<

GCTGCTCCAGTCAACACTACAACAGAAGATGAAACGGCACAAATTCCGGCTGAAGCTGTC
15  ---------+---------+---------+---------+---------+---------+
    CGACGAGGTCAGTTGTGATGTTGTCTTCTACTTTGCCGTGTTTAAGGCCGACTTCGACAG
    AlaAlaProValAsnThrThrThrGluAspGluThrAlaGlnIleProAlaGluAlaVal
    <<<<<<<<<<<<<<<<<<<<<<<<<<<<<<<<<<<<<<<<<<<<<<<<<<<<<<<<<<<

ATCGGTTACTCAGATTTAGAAGGGGATTTCGATGTTGCTGTTTTGCCATTTTCCAACAGC
20  ---------+---------+---------+---------+---------+---------+
    TAGCCAATGAGTCTAAATCTTCCCCTAAAGCTACAACGACAAAACGGTAAAAGGTTGTCG
    IleGlyTyrSerAspLeuGluGlyAspPheAspValAlaValLeuProPheSerAsnSer
    <<<<<<<<<<α-factor-prepro leader sequence 1-81<<<<<<<<<<<<<

ACAAATAACGGGTTATTGTTTATAAATACTACTATTGCCAGCATTGCTGCTAAAGAAGAA
25  ---------+---------+---------+---------+---------+---------+
    TGTTTATTGCCCAATAACAAATATTTATGATGATAACGGTCGTAACGACGATTTCTTCTT
    ThrAsnAsnGlyLeuLeuPheIleAsnThrThrIleAlaSerIleAlaAlaLysGluGlu
    <<<<<<<<<<<<<<<<<<<<<<<<<<<<<<<<<<<<<<<<<<<<<<<<<<<<<<<<<<<
             NcoI
30  GGGGTATCCATGGCTAAGAGATTCGTTAACCAACACTTGTGCGGTTCCCACTTGGTTGAA
    ---------+---------+---------+---------+---------+---------+
    CCCCATAGGTACCGATTCTCTAAGCAATTGGTTGTGAACACGCCAAGGGTGAACCAACTT
    GlyValSerMetAlaLysArgPheValAsnGlnHisLeuCysGlySerHisLeuValGlu
    <<<<<<<<           >>>>>>>>>>>>>>>>>>>>>>>>>>>>>>>>>>>>>>>>
35  HindIII
    GCTTTGTACTTGGTTTGTGGTGAAAGAGGTTTCTTCTACACTGACAAGGATGCTAAGGGT
```

FIG. 2

```
          ---------+---------+---------+---------+---------+---------+
          CGAAACATGAACCAAACACCACTTTCTCCAAAGAAGATGTGACTGTTCCGACGATTCCCA
          AlaLeuTyrLeuValCysGlyGluArgGlyPhePheTyrThrAspLysAlaAlaLysGly
          >>>>>>Insulin Precursor B₁₋₂₇-Asp-Lys-Ala-Ala-Lys-A₁₋₂₁>>>>>>>

5        ATCGTTGAACAATGTTGTACTTCTATCTGTTCTTTGTACCAATTGGAAAACTACTGTAAC
          ---------+---------+---------+---------+---------+---------+
          TAGCAACTTGTTACAACATGAAGATAGACAAGAAACATGGTTAACCTTTTGATGACATTG
          IleValGluGlnCysCysThrSerIleCysSerLeuTyrGlnLeuGluAsnTyrCysAsn
          >>>>>>>>>>>>>>>>>>>>>>>>>>>>>>>>>>>>>>>>>>>>>>>>>>>>>>>>>>>>
10                    XbaI
          TAGACGCAGCCCGCAGGCTCTAGAAACTAAGATTAATATAATTATATAAAAATATTATCT
          ---------+---------+---------+---------+---------+---------+
          ATCTGCGTCGGGCGTCCGAGATCTTTGATTCTAATTATATTAATATATTTTTATAATAGA

TCTTTTCTTTATATCTAGTGTTATGTAAAATAAATTGATGACTACGGAAAGCTAGCTTTT
15        ---------+---------+---------+---------+---------+---------+
          AGAAAAGAAATATAGATCACAATACATTTTATTTAACTACTGATGCCTTTCGATCGAAAA
                                                     P2
```

FIG. 3

```
                                                                EcoRI
         TGTTTGTATTCTTTTCTTGCTTAAATCTATAACTACAAAAAACACATACAGGAATTCCAT
         ---------+---------+---------+---------+---------+---------+
    5    ACAAACATAAGAAAAGAACGAATTTAGATATTGATGTTTTTTGTGTATGTCCTTAAGGTA

TCAAGAATAGTTCAAACAAGAAGATTACAAACTATCAATTTCATACACAATATAAACGAC
         ---------+---------+---------+---------+---------+---------+
         AGTTCTTATCAAGTTTGTTCTTCTAATGTTTGATAGTTAAAGTATGTGTTATATTTGCTG

10    GGTACCAAAATAATGAAACTGAAAACTGTAAGATCTGCGGTCCTTTCGTCACTCTTTGCA
         ---------+---------+---------+---------+---------+---------+
         CCATGGTTTTATTACTTTGACTTTTGACATTCTAGACGCCAGGAAAGCAGTGAGAAACGT
                     MetLysLeuLysThrValArgSerAlaValLeuSerSerLeuPheAla
                     <<<<<<<<YAP3 (pre) signal peptide<<<<<<<<<<<<<<<

15    TCTCAGGTCCTTGGCCAACCAATTGACGACACTGAATCTAACACTACTTCTGTCAACTTG
         ---------+---------+---------+---------+---------+---------+
         AGAGTCCAGGAACCGGTTGGTTAACTGCTGTGACTTAGATTGTGATGAAGACAGTTGAAC
         SerGlnValLeuGlyGlnProIleAspAspThrGluSerAsnThrThrSerValAsnLeu
         <<<<<<<<<<<<<<<<<<********************************************
   20                                                             NcoI
         ATGGCTGACGACACTGAATCTATCAACACTACTTTGGTTAACTTGGCTAACGTTGCCATG
         ---------+---------+---------+---------+---------+---------+
         TACCGACTGCTGTGACTTAGATAGTTGTGATGAAACCAATTGAACCGATTGCAACGGTAC
         MetAlaAspAspThrGluSerIleAsnThrThrLeuValAsnLeuAlaAsnValAlaMet
   25    ***********S1$_{PAVA}$(pro) leader peptide*********************

GCTCCAGCTCCAGCTAAGAGACATGCTGAAGGTACCTTCACCTCTGACGTCTCGAGTTAC
         ---------+---------+---------+---------+---------+---------+
         CGAGGTCGAGGTCGATTCTCTGTACGACTTCCATGGAAGTGGAGACTGCAGAGCTCAATG
         AlaProAlaValAlaLysArgHisAlaGLuGLyThrPreThrSerAspValSerSerTyr
   30    ***********************>>>>>>>>>>>>>>>>>>>>>>>>>>>>>>>>>>>>>>>
                                                                  XbaI
         TTGGAAGGCCAAGCTGCTAAGGAGTTCATCGCTTGGTTGGTTAAGGGCGCTTAGTCTAGA
         ---------+---------+---------+---------+---------+---------+
         AACCTTCCGGTTCGACGATTCCTCAAGTAGCGAACCAACCAATTCCCGCGAATCAGATCT
   35    LeuGluGlyGlnAlaAlaLysGluPheIleAlaTrpLeuValLysGlyAla
         >>>>>>>>>>>>>>>>GLP-1$_{7-36Ala}$>>>>>>>>>>>>>>>>>>>>>>>>>>>

AACTAAGATTAATATAATTATATAAAAATATTATCTTCTTTTCTTTATATCTAGTGTTAT
         ---------+---------+---------+---------+---------+---------+
         TTGATTCTAATTATATTAATATATTTTTATAATAGAAGAAAAGAAATATAGATCACAATA

GTAAAATAAATTGATGACTACGGAAAGCTAGCTTTT
         ---------+---------+---------+------
         CATTTTATTTAACTACTGATGCCTTTCGATCGAAAA
                P2
```

FIG. 4

```
                                                             EcoRI
     GTTTGTATTCTTTTCTTGCTTAAATCTATAACTACAAAAAACACATACAGGAATTCCATT
     ---------+---------+---------+---------+---------+---------+
 5   CAAACATAAGAAAAGAACGAATTTAGATATTGATGTTTTTTGTGTATGTCCTTAAGGTAA

CAAGAATAGTTCAAACAAGAAGATTACAAACTATCAATTTCATACACAATATAAACGATT
     ---------+---------+---------+---------+---------+---------+
     GTTCTTATCAAGTTTGTTCTTCTAATGTTTGATAGTTAAAGTATGTGTTATATTTGCTAA

AAAAGAATGAGATTTCCTTCAATTTTTACTGCAGTTTTATTCGCAGCATCCTCCGCATAA
10   ---------+---------+---------+---------+---------+---------+
     TTTTCTTACTCTAAAGGAAGTTAAAAATGACGTCAAAATAAGCGTCGTAGGAGGCGTAAT
             MetArgPheProSerIlePheThrAlaValPheAlaAlaSerSerAlaLeu
     <<<<<<<<<<<<<<<<<<<<<<<<<<<<<<<<<<<<<<<<<<<<<<<<<<<<<<<<<<<

GCTGCTCCAGTCAACACTACAACAGAAGATGAAACGGCACAAATTCCGGCTGAAGCTGTC
15   ---------+---------+---------+---------+---------+---------+
     CGACGAGGTCAGTTGTGATGTTGTCTTCTACTTTGCCGTGTTTAAGGCCGACTTCGACAG
     AlaAlaProValAsnThrThrThrGluAspGluThrAlaGlnIleProAlaGluAlaVal
     <<<<<<<<<<<<<<<<<<<<<<<<<<<<<<<<<<<<<<<<<<<<<<<<<<<<<<<<<<<

ATCGGTTACTCAGATTTAGAAGGGGATTTCGATGTTGCTGTTTTGCCATTTTCCAACAGC
20   ---------+---------+---------+---------+---------+---------+
     TAGCCAATGAGTCTAAATCTTCCCCTAAAGCTACAACGACAAAACGGTAAAAGGTTGTCG
     IleGlyTyrSerAspLeuGluGlyAspPheAspValAlaValLeuProPheSerAsnSer
     <<<<<<<<<<α-factor-prepro leader sequence 1-81<<<<<<<<<<<<<<

ACAAATAACGGGTTATTGTTTATAAATACTACTATTGCCAGCATTGCTGGTAAAGAAGAA
25   ---------+---------+---------+---------+---------+---------+
     TGTTTATTGCCCAATAACAAATATTTATGATGATAACGGTCGTAACGACGATTTCTTCTT
     ThrAsnAsnGlyLeuLeuPheIleAsnThrThrIleAlaSerIleAlaAlaLysGluGlu
     <<<<<<<<<<<<<<<<<<<<<<<<<<<<<<<<<<<<<<<<<<<<<<<<<<<<<<<<<<<
             NcoI
30   GGGGTAGCCATGGCTAAGAGATTCGTTAACCAACACTTGTGCGGTTCCCACTTGGTTGAA
     ---------+---------+---------+---------+---------+---------+
     CCCCATAGGTACCGATTCTCTAAGCAATTGGTTGTGAACACGCCAAGGGTGAACCAACTT
     GlyValSerMetAlaLysArgPheValAsnGlnHisLeuCysGlySerHisLeuValGlu
     <<<<<<<<<           >>>>>>>>>>>>>>>>>>>>>>>>>>>>>>>>>>>>>>>
35   HindIII
     GCTTTGTACTTGGTTTGCGGTGAAAGAGGTTTCTTCTACACTCCTAAGGCTGCTAGAGGT
     ---------+---------+---------+---------+---------+---------+
```

FIG. 5

```
CGAAACATGAACCAAACGCCACTTTCTCCAAAGAAGATGTGAGGATTCCGACGATCTCCA
AlaLeuTyrLeuValCysGlyGluArgGlyPhePheTyrThrProLysAlaAlaArgGly
>>>>>>Insulin Precursor B₁₋₂₉-Ala-Ala-Arg-A₁₋₂₁ >>>>>>>>>>>>>>>

ATTGTCGAACAATGCTGTACCTCCATCTGCTCCTTGTACCAATTGGAAAACTACTGCAAC
5    ----------+---------+---------+---------+---------+---------+
     TAACAGCTTGTTACGACATGGCGGTAGACGAGGAACATGGTTAACCTTTTGATGACGTTG
     IleValGluGlnCysCysThrSerIleCysSerLeuTyrGlnLeuGluAsnTyrCysAsn
     >>>>>>>>>>>>>>>>>>>>>>>>>>>>>>>>>>>>>>>>>>>>>>>>>>>>>>>>>>>>
                     XbaI
10   TAGACGCAGCCCGCAGGCTCTAGAAACTAAGATTAATATAATTATATAAAAATATTATCT
     ----------+---------+---------+---------+---------+---------+
     ATCTGCGTCGGGCCTCCGAGATCTTTGATTCTAATTATATTAATATATTTTTATAATAGA

TCTTTTCTTTATATCTAGTGTTATGTAAAATAAATTGATGACTACGGAAAGCTAGCTTTT
     ----------+---------+---------+---------+---------+---------+
15   AGAAAAGAAATATAGATCACAATACATTTTATTTAACTACTGATGCCTTTCGATCGAAAA
                       P2
```

FIG. 6

```
                                                            EcoRI
    TGTTTGTATTCTTTTCTTGCTTAAATCTATAACTACAAAAAACACATACAGGAATTCCAT
    ----------+---------+---------+---------+---------+---------+
 5  ACAAACATAAGAAAGAACGAATTTAGATATTGATGTTTTTTGTGTATGTCCTTAAGGTA

TCAAGAATAGTTCAAACAAGAAGATTACAAACTATCAATTTCATACACAATATAAACGAC
    ----------+---------+---------+---------+---------+---------+
    AGTTCTTATCAAGTTTGTTCTTCTAATGTTTGATAGTTAAAGTATGTGTTATATTTGCTG

10  GGTACCAAAATAATGAAACTGAAAACTGTAAGATCTGCGGTCCTTTCGTCACTCTTTGCA
    ----------+---------+---------+---------+---------+---------+
    CCATGGTTTTATTACTTTGACTTTTGACATTCTAGACGCCAGGAAAGCAGTGAGAAACGT
              MetLysLeuLysThrValArgSerAlaValLeuSerSerLeuPheAla
              <<<<<<<<YAP3 (pre) signal peptid<<<<<<<<<<<<<<<

15  TCTCAGGTCCTTGGCCAACCAATTGACGACACTGAATCTAACACTACTTCTGTCAACTTG
    ----------+---------+---------+---------+---------+---------+
    AGAGTCCAGGAACCGGTTGGTTAACTGVTGTGACTTTAGTTGTGATGAAGACAGTTGAAC
    SerGlnValLeuGlyGlnProIleAspAspThrGluSerAsnThrThrSeValAsnLeu
    <<<<<<<<<<<<<<<<<*******************************************
20             XbaI
    ATGGCTGACGACACTGAATCTAGATTCGCTACTAACACTACTTTGGCTTTGGATGTTGTT
    ----------+---------+---------+---------+---------+---------+
    TACCGACTGCTGTGACTTAGATCTAAGCGATGATTGTGATGAAACCGAAACCTACAACAA
    MetAlaAspAspThrGluSerArgPheAlaThrAsnThrThrLeuAlaLeuAspValVal
25  ************LA19 (pro) leader peptide*********************
              NcoI
    AACTTGATCTCCATGGCTAAGAGATTCGTTAACCAACACTTGTGCGGTTCCCACTTGGTT
    ----------+---------+---------+---------+---------+---------+
    TTGAACGAGAGGTACCGATTCTCTAAGCAATTGGTTGTGAACACGCCAAGGGTGAACCAA
30  AsnLeuIleSerMetAlaLysArgPheValAsnGlnHisLeuCysGlySerHisLeuVal
    *********************>>>>>>>>>>>>>>>>>>>>>>>>>>>>>>>>>>>>>>>
    HindIII
    GAAGCTTTGTACTTGGTTTGCGGTGAAAGAGGTTTCTTCTACACTCCTAAGGCTGCTAAG
35  ----------+---------+---------+---------+---------+---------+
    CTTCGAAACATGAACCAAACGCCACTTTCTCCAAAGAAGATGTGAGGATTCCGACGATTC
    GluAlaLeuTyrLeuValCysGlyGluArgGlyPhePheTyrThrProLysAlaAlaLys
    >>>>>>>>>Insulin Precursor B₁₋₂₉-Ala-Ala-Lys-A₁₋₂₉>>>>>>>>>
    GGTATTGTCGAACAATGCTGTACCTCCATCTGCTCCTTGTACCAATTGGAAAACTACTGC
40  ----------+---------+---------+---------+---------+---------+
```

FIG. 7

```
    CCATAACAGCTTGTTACGACATGGAGGTAGACGAGGAACATGGTTAACCTTTTGATGACG
    GlyIleValGluGlnCysCysThrSerIleCysSerLeuTyrGlnLeuGluAsnTyrCys
    >>>>>>>>>>>>>>>>>>>>>>>>>>>>>>>>>>>>>>>>>>>>>>>>>>>>>>>>>>>>
                              XbaI
5   AACTAGACGCAGCCCGCAGGCTCTAGAAACTAAGATTAATATAATTATATAAAAATATTA
    ---------+---------+---------+---------+---------+---------+
    TTGATCTGCGTCGGGCGTCCGAGATCTTTGATTCTAATTATATTAATATATTTTTATAAT
    Asn
    >>>

10  TCTTCTTTTCTTTATATCTAGTGTTATGTAAAATAAATTGATGACTACGGAAAGCTAGCT
    ---------+---------+---------+---------+---------+---------+
    AGAAGAAAAGAAATATAGATCACAATACATTTTATTTAACTACTGATGCCTTTCGATCGA
                         P2
```

FIG. 8

Peak M: Background profile on yeast growth media
Peak A: B$_{chain}$(1-27)-Asp-Lys-Ala-Ala-Lys-A$_{chain}$(1-21)
Peak D: Glu-Glu-Ala-Glu-Ala-Glu-Ala-Pro-Lys-B$_{chain}$(1-27)-Asp-Lys-Ala-Ala-Lys-A$_{chain}$(1-21)

pAK729_LA19_X5_MI3.POT

```
                  1
                  M   K    L   K    T   V     R   S    A   V   L   S
                                            BglII
                                            -------
               ATGAAA    CTGAAAACTG   TAAGATCTGC   GGTCCTTTCG
               TACTTT    GACTTTTGAC   ATTCTAGACG   CCAGGAAAGC

S   L   F  A    S  Q   V     L  G   Q     P  I   D   D      T  E   S
TCACTCTTTG   CATCTCAGGT   CCTTGGCCAA   CCAATTGACG   ACACTGAATC
AGTGAGAAAC   GTAGAGTCCA   GGAACCGGTT   GGTTAACTGC   TGTGACTTAG

N   T   T     S   V   N   L     M   A   D       D   T   E      S   R   F
                                                                    XbaI
                                                                    -------
TAACACTACT   TCTGTCAACT   TGATGGCTGA   CGACACTGAA   TCTAGATTCG
ATTGTGATGA   AGACAGTTGA   ACTACCGACT   GCTGTGACTT   AGATCTAAGC

A   T   N   T    T   D   A     L   D   V   V     N   G   I       S   M   A
                                                                    NcoI
                                                                    -------
CTACTAACAC   TACTTTGGCT   TTGGATGTTG   TTAACTTGAT   CTCCATGGCT
GATGATTGTG   ATGAAACCGA   AACCTACAAC   AATTGAACTA   GAGGTACCGA

K   R   E   E      A   E   F       K   E   V      N   Q   H   L    C   G   S
AAGAGAGAAG   AAGCTGAACC   AAAGTTCGTT   AACCAACACT   TGTGCGGTTC
TTCTCTCTTC   TTCGACTTGG   TTTCAAGCAA   TTGGTTGTGA   ACACGCCAAG

H   L   V     E   A   L   Y      L   V   C      G   E   R      G   F   F
CCACTTGGTT   GAAGCTTTGT   ACTTGGTTTG   CGGTGAAAGA   GGTTTCTTCT
GGTGAACCAA   CTTCGAAACA   TGAACCAAAC   GCCACTTTCT   CCAAAGAAGA

Y   T   P   K     A   A   K      G   I   V   E       Q   C   C      T   S   I
ACACTCCTAA   GGCTGCTAAG   GGTATTGTCG   AACAATGCTG   TACCTCCATC
TGTGAGGATT   CCGACGATTC   CCATAACAGC   TTGTTACGAC   ATGGAGGTAG
                                                                    123
   C   S   L   Y     Q   L   E       N   Y   C      N    *
TGCTCCTTGT   ACCAATTGGA   AAACTACTGC   AACTAGACGC   AGCCCGCAGG
ACGAGGAACA   TGGTTAACCT   TTTGATGACG   TTGATCTGCG   TCGGGCGTCC

XbaI
-------
CTCTAGA
GAGATCT
```

FIG. 14

```
                                                                    EcoRI
                                                                    -------
        TTCTTGCTTA  AATCTATAAC  TACAAAAAAC  ACATACAGGA  ATTCCATTCA
        AAGAACGAAT  TTAGATATTG  ATGTTTTTTG  TGTATGTCCT  TAAGGTAAGT
        AGAATAGTTC  AAACAAGAAG  ATTACAAACT  ATCAATTTCA  TACACAATAT
        TCTTATCAAG  TTTGTTCTTC  TAATGTTTGA  TAGTTAAAGT  ATGTGTTATA
    +1                    M K  L K T V     R S  A      V L S
                                            BglII
                                            -------
        AAACGATTAA  AAGAATGAAA  CTGAAAACTG  TAAGATCTGC  GGTCCTTTCG
        TTTGCTAATT  TTCTTACTTT  GACTTTGAC   ATTCTAGACG  CCAGGAAAGC
    +1  S L F A     S Q V       L G Q       P I D D     T E S
                                StyI
                                -------
        TCACTCTTTG  CATCTCAGGT  CCTTGGCCAA  CCAATTGACG  ACACTGAATC
        AGTGAGAAAC  GTAGAGTCCA  GGAACCGGTT  GGTTAACTGC  TGTGACTTAG
    +1    N T T    S V N L     M A D       D T E       S R F
                                                        XbaI
                                                        ------
        TAACACTACT  TCTGTCAACT  TGATGGCTGA  CGACACTGAA  TCTAGATTCG
        ATTGTGATGA  AGACAGTTGA  ACTACCGACT  GCTGTGACTT  AGATCTAAGC
    +1  A T N T     T L A       L D V V     N L I       S M A
                                                        StyI
                                                        -------
                                                        NcoI
                                                        -------
        CTACTAACAC  TACTTTGGCT  TTGGATGTTG  TTAACTTGAT  CTCCATGGCT
        GATGATTGTG  ATGAAACCGA  AACCTACAAC  AATTGAACTA  GAGGTACCGA
    +1  K R E E     A E P       K F V       N Q H L     C G S
        AAGAGAGAAG  AAGCTGAACC  AAAGTTCGTT  AACCAACACT  TGTGCGGTTC
        TTCTCTCTTC  TTCGACTTGG  TTTCAAGCAA  TTGGTTGTGA  ACACGCCAAG
    +1   H L V      E A L Y     L V C       G E R       G F F
                    HindIII
                    ----------
        CCACTTGGTT  GAAGCTTTGT  ACTTGGTTTG  CGGTGAAAGA  GGTTTCTTCT
        GGTGAACCAA  CTTCGAAACA  TGAACCAAAC  GCCACTTTCT  CCAAAGAAGA
    +1   Y T ? K    G I V       E Q C C     T S I       C S L
             Bsu36I
             ----------
        ACACTCCTAA  GGGTATTGTC  GAACAATGCT  GTACCTCCAT  CTGCTCCTTG
        TGTGAGGATT  CCCATAACAG  CTTGTTACGA  CATGGAGGTA  GACGAGGAAC
    +1   Y Q L E    N Y C       N *
                                                        XbaI
                                                        ------
        TACCAATTGG  AAAACTACTG  CAACTAGACG  CAGCCCGCAG  GCTCTAGAAA
        ATGGTTAACC  TTTTGATGAC  GTTGATCTGC  GTCGGGCGTC  CGAGATCTTT
```

FIG. 16

```
                                                                    EcoRI
                                                                    -------
             TTCTTGCTTA   AATCTATAAC   TACAAAAAAC   ACATACAGGA   ATTCCATTCA
             AAGAACGAAT   TTAGATATTG   ATGTTTTTTG   TGTATGTCCT   TAAGGTAAGT
             AGAATAGTTC   AAACAAGAAG   ATTACAAACT   ATCAATTTCA   TACACAATAT
             TCTTATCAAG   TTTGTTCTTC   TAATGTTTGA   TAGTTAAAGT   ATGTGTTATA
      +1                       M  K    L  K  T  V    R  S  A    V  L  S
                                                        BglII
                                                        -------
             AAACGATTAA   AAGAATGAAA   CTGAAAACTG   TAAGATCTGC   GGTCCTTTCG
             TTTGCTAATTT  TTCTTACTTT   GACTTTTGAC   ATTCTAGACG   CCAGGAAAGC
      +1    S  L  F  A    S  Q  V      L  G  Q      P  I  D  D   T  E  S
                                      StyI
                                      -------
             TCACTCTTTG   CATCTCAGGT   CCTTGGCCAA   CCAATTGACG   ACACTGAATC
             AGTGAGAAAC   GTAGAGTCCA   GGAACCGGTT   GGTTAACTGC   TGTGACTTAG
      +1       N  T  T    S  V  N  L   M  A  D      D  T  E      S  R  F
                                                                    XbaI
                                                                    ------
             TAACACTACT   TCTGTCAACT   TGATGGCTGA   CGACACTGAA   TCTAGATTCG
             ATTGTGATGA   AGACAGTTGA   ACTACCGACT   GCTGTGACTT   AGATCTAAGC
      +1   A  T  N  T     T  L  A      L  D  V  V    N  L  I     S  M  A
                                                                    StyI
                                                                    -------
                                                                    NcoI
                                                                    -------
             CTACTAACAC   TACTTTGGCT   TTGGATGTTG   TTAACTTGAT   CTCCATGGCT
             GATGATTGTG   ATGAAACCGA   AACCTACAAC   AATTGAACTA   GAGGTACCGA
      +1    K  R  E  E     A  E  P     K  F  V      N  Q  H  L    C  G  S

AAGAGAGAAG   AAGCTGAACC   AAAGTTCGTT   AACCAACACT   TGTGCGGTTC
             TTCTCTCTTC   TTCGACTTGG   TTTCAAGCAA   TTGGTTGTGA   ACACGCCAAG
      +1      H  L  V      E  A  L  Y    L  V  C     G  E  R      G  F  F
                         HindIII
                         ----------
             CCACTTGGTT   GAAGCTTTGT   ACTTGGTTTG   CGGTGAAAGA   GGTTTCTTCT
             GGTGAACCAA   CTTCGAAACA   TGAACCAAAC   GCCACTTTCT   CCAAAGAAGA
      +1      Y  T  P  K   S  D  D     A  K  G  I    V  E  Q     C  C  T
             ACACTCCTAA   GTCTGACGAT   GCTAAGGGTA   TTGTCGAGCA   ATGCTGTACC
             TGTGAGGATT   CAGACTGCTA   CGATTCCCAT   AACAGCTCGT   TACGACATGG
      +1    S  I  C  S     L  Y  Q     L  E  N      Y  C  N  *
             TCCATCTGCT   CCTTGTACCA   ATTGGAAAAC   TACTGCAACT   AGACGCAGCC
             AGGTAGACGA   GGAACATGGT   TAACCTTTTG   ATGACGTTGA   TCTGCGTCGG
                            XbaI
                            ------
             CGCAGGCTCT   AGAAACTAAG   ATTAATATAA   TTATATAAAA   ATATTATCTT
             GCGTCCGAGA   TCTTTGATTC   TAATTATATT   AATATATTTT   TATAATAGAA
```

FIG. 17

```
                                                                    EcoRI
                                                                    -------
          TTCTTGCTTA  AATCTATAAC  TACAAAAAAC  ACATACAGGA  ATTCCATTCA
          AAGAACGAAT  TTAGATATTG  ATGTTTTTTG  TGTATGTCCT  TAAGGTAAGT
          AGAATAGTTC  AAACAAGAAG  ATTACAAACT  ATCAATTTCA  TACACAATAT
          TCTTATCAAG  TTTGTTCTTC  TAATGTTTGA  TAGTTAAAGT  ATGTGTTATA
     +1                   M  K   L  K  T  V   R  S  A    V  L  S
                                              BglII
          AAACGATTAA  AAGAATGAAA  CTGAAAACTG  TAAGATCTGC  GGTCCTTTCG
          TTTGCTAATTT TTCTTACTTT GACTTTTGAC  ATTCTAGACG  CCAGGAAAGC
     +1    S  L  F  A   S  Q  V   L  G  Q    P  I  D  D    T  E  S
                                StyI
          TCACTCTTTG  CATCTCAGGT  CCTTGGCCAA  CCAATTGACG  ACACTGAATC
          AGTGAGAAAC  GTAGAGTCCA  GGAACCGGTT  GGTTAACTGC  TGTGACTTAG
     +1    N  T  T   S  V  N  L   M  A  D     D  T  E    S  R  F
                                                          XbaI
                                                          -------
          TAACACTACT  TCTGTCAACT  TGATGGCTGA  CGACACTGAA  TCTAGATTCG
          ATTGTGATGA  AGACAGTTGA  ACTACCGACT  GCTGTGACTT  AGATCTAAGC
     +1   A  T  N  T    T  L  A   L  D  V  V    N  L  I   S  M  A
                                                          StyI
                                                          NcoI
                                                          -------
          CTACTAACAC  TACTTTGGCT  TTGGATGTTG  TTAACTTGAT  CTCCATGGCT
          GATGATTGTG  ATGAAACCGA  AACCTACAAC  AATTGAACTA  GAGGTACCGA
     +1   K  R  E  E      A  E  P    K  F  V    N  Q  H  L    C  G  S
          AAGAGAGAAG  AAGCTGAACC  AAAGTTCGTT  AACCAACACT  TGTGCGGTTC
          TTCTCTCTTC  TTCGACTTGG  TTTCAAGCAA  TTGGTTGTGA  ACACGCCAAG
     +1    H  L  V    E  A  L  Y    L  V  C    G  E  R    G  F  F
                      HindIII
                      ----------
          CCACTTGGTT  GAAGCTTTGT  ACTTGGTTTG  CGGTGAAAGA  GGTTTCTTCT
          GGTGAACCAA  CTTCGAAACA  TGAACCAAAC  GCCACTTTCT  CCAAAGAAGA
     +1    Y  T  D  K    A  A  K   G  I  V  E    Q  C  C    T  S  I
          ACACTGACAA  GGCTGCTAAG  GGTATTGTTG  AACAATGTTG  TACCTCTATC
          TGTGACTGTT  CCGACGATTC  CCATAACAAC  TTGTTACAAC  ATGGAGATAG
     +1    C  S  L  Y   Q  L  E    N  Y  C    N  *
          TGTTCTTTGT  ACCAATTGGA  AAACTACTGT  AACTAGACGC  AGCCCGCAGG
          ACAAGAAACA  TGGTTAACCT  TTTGATGACA  TTGATCTGCG  TCGGGCGTCC
          XbaI
          -----
          CTCTAGACTA  AGATTAATAT  AATTATATAA  AAATATTATC  TTCTTTTCTT
          GAGATCTGAT  TCTAATTATA  TTAATATATT  TTTATAATAG  AAGAAAAGAA
           XbaI
           -----
          AGGCTCTAGA  AACTAAGATT  AATATAATTA  TATAAAAATA  TTATCTTCTT
          TCCGAGATCT  TTGATTCTAA  TTATATTAAT  ATATTTTTAT  AATAGAAGAA
```

FIG. 18

Gln Pro Ile Asp Asp Thr Glu Ser Asn Thr Thr Ser Val Asn Leu Met
            5                   10                  15

Ala Asp Asp Thr Glu Ser Arg Phe Ala Thr Asn Thr Thr Leu Ala Leu
            20                  25                  30

Asp Val Val Asn Leu Ile Ser Met Ala Lys Arg
            35                  40

FIG. 19 pAK721_LA19_X5_MI3_OMC.POT

```
                                                          EcoRI
                                                          -------
 901  TTCTTGCTTA  AATCTATAAC  TACAAAAAAC  ACATACAGGA  ATTCCATTCA
      AAGAACGAAT  TTAGATATTG  ATGTTTTTTG  TGTATGTCCT  TAAGGTAAGT
 951  AGAATAGTTC  AAACAAGAAG  ATTACAAACT  ATCAATTTCA  TACACAATAT
      TCTTATCAAG  TTTGTTCTTC  TAATGTTTGA  TAGTTAAAGT  ATGTGTTATA
 +1                      M K  L K T V     R S A       V L S
                                          BglII
1001  AAACGATTAA  AAGAATGAAA  CTGAAAACTG  TAAGATCTGC  GGTCCTTTCG
      TTTGCTAATT  TTCTTACTTT  GACTTTTGAC  ATTCTAGACG  CCAGGAAAGC
 +1    S L F A    S Q V       L G Q       P I D D     T E S
1051  TCACTCTTTG  CATCTCAGGT  CCTTGGCCAA  CCAATTGACG  ACACTGAATC
      AGTGAGAAAC  GTAGAGTCCA  GGAACCGGTT  GGTTAACTGC  TGTGACTTAG
 +1      N T T   S V N L      M A D       D T E       S R F
                                                      XbaI
                                                      -------
1101  TAACACTACT  TCTGTCAACT  TGATGGCTGA  CGACACTGAA  TGTAGATTCG
      ATTGTGATGA  AGACAGTTGA  ACTACCGACT  GCTGTGACTT  AGATCTAAGC
 +1   A T N T     T L A L D V V           N L I       S M A
                                                      NcoI
                                                      -------
1151  CTACTAACAC  TACTTTGGCT  TTGGATGTTG  TTAACTTGAT  CTCCATGGCT
      GATGATTGTG  ATGAAACCGA  AACCTACAAC  AATTGAACTA  GAGGTACCGA
 +1    K R E E    G E P       K F V N Q H L           C G S
1201  AAGAGAGAAG  AAGGTGAACC  AAAGTTCGTT  AACCAACACT  TGTGCGGTTC
      TTCTCTCTTC  TTCCACTTGG  TTTCAAGCAA  TTGGTTGTGA  ACACGCCAAG
 +1       H L V   E A L Y     L V C       G E R       G F F
              HindIII
              -------
1251  CCACTTGGTT  GAAGCTTTGT  ACTTGGTTTG  CGGTGAAAGA  GGTTTCTTCT
      GGTGAACCAA  CTTCGAAACA  TGAACCAAAC  GCCACTTTCT  CCAAAGAAGA
 +1    Y T P K    A A K G I V E           Q C C       T S I
1301  ACACTCCTAA  GGCTGCTAAG  GGTATTGTCG  AACAATGCTG  TACCTCCATC
      TGTGAGGATT  CCGACGATTC  CCATAACAGC  TTGTTACGAC  ATGGAGGTAG
 +1    C S L Y    Q L E       N Y C       N *
1351  TGCTCCTTGT  ACCAATTGGA  AAACTACTGC  AACTAGACGC  AGCCCGCAGG
      ACGAGGAACA  TGGTTAACCT  TTTGATGACG  TTGATCTGCG  TCGGGCGTCC
      XbaI
      -----
1401  CTCTAGAAAC  TAAGATTAAT  ATAATTATAT  AAAAATATTA  TCTTCTTTTC
      GAGATCTTTG  ATTCTAATTA  TATTAATATA  TTTTTATAAT  AGAAGAAAAG
```

FIG. 21

SEQUENCE LISTING

<160> NUMBER OF SEQ ID NOS: 93

<210> SEQ ID NO 1
<211> LENGTH: 6
<212> TYPE: PRT
<213> ORGANISM: Artificial Sequence
<220> FEATURE:
<223> OTHER INFORMATION: Variation

<400> SEQUENCE: 1

Glu Glu Ala Glu Pro Lys
 1               5

<210> SEQ ID NO 2
<211> LENGTH: 6
<212> TYPE: PRT
<213> ORGANISM: Artificial Sequence
<220> FEATURE:
<223> OTHER INFORMATION: Variation

<400> SEQUENCE: 2

Glu Glu Gly Glu Pro Lys
 1               5

<210> SEQ ID NO 3
<211> LENGTH: 15
<212> TYPE: PRT
<213> ORGANISM: Artificial Sequence
<220> FEATURE:
<223> OTHER INFORMATION: Variation

<400> SEQUENCE: 3

Gln Pro Ile Asp Glu Asp Asn Asp Thr Ser Val Asn Leu Pro Ala
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Variation

<400> SEQUENCE: 4

Gln Pro Ile Asp Asp Glu Asn Thr Thr Ser Val Asn Leu Pro Ala
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Variation

<400> SEQUENCE: 5

Gln Pro Ile Asp Asp Glu Ser Asn Thr Thr Ser Val Asn Leu Pro Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Variation

<400> SEQUENCE: 6

Gln Pro Ile Asp Asp Glu Asn Thr Thr Ser Val Asn Leu Pro Val
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Variation

<400> SEQUENCE: 7

Gln Pro Ile Asp Asp Glu Asn Thr Thr Ser Val Asn Leu Pro Val
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Variation

<400> SEQUENCE: 8

Gln Pro Ile Asp Asp Thr Glu Ser Asn Thr Thr Ser Val Asn Leu Pro
1               5                   10                  15

Ala

<210> SEQ ID NO 9
<211> LENGTH: 15
<212> TYPE: PRT
<213> ORGANISM: Artificial Sequence
<220> FEATURE:
<223> OTHER INFORMATION: Variation

<400> SEQUENCE: 9

Gln Pro Ile Asp Asp Glu Asn Thr Thr Ser Val Asn Leu Met Ala
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: Variation

<400> SEQUENCE: 10

Gln Pro Ile Asp Asp Thr Glu Ser Asn Thr Thr Ser Val Asn Leu Pro
1               5                   10                  15

Gly Ala

<210> SEQ ID NO 11
<211> LENGTH: 17
<212> TYPE: PRT
<213> ORGANISM: Artificial Sequence
<220> FEATURE:
<223> OTHER INFORMATION: Variation

<400> SEQUENCE: 11

Gln Pro Ile Asp Asp Thr Glu Ser Asn Thr Thr Ser Val Asn Leu Met
1               5                   10                  15

Ala

<210> SEQ ID NO 12
<211> LENGTH: 17
<212> TYPE: PRT
<213> ORGANISM: Artificial Sequence

```
<220> FEATURE:
<223> OTHER INFORMATION: Variation

<400> SEQUENCE: 12

Gln Pro Ile Asp Asp Thr Glu Ser Asn Thr Thr Ser Val Asn Val Pro
 1               5                  10                  15

Thr

<210> SEQ ID NO 13
<211> LENGTH: 17
<212> TYPE: PRT
<213> ORGANISM: Artificial Sequence
<220> FEATURE:
<223> OTHER INFORMATION: Variation

<400> SEQUENCE: 13

Gln Pro Ile Asp Asp Thr Glu Ser Asn Thr Thr Leu Val Asn Val Pro
 1               5                  10                  15

Thr

<210> SEQ ID NO 14
<211> LENGTH: 17
<212> TYPE: PRT
<213> ORGANISM: Artificial Sequence
<220> FEATURE:
<223> OTHER INFORMATION: Variation

<400> SEQUENCE: 14

Gln Pro Ile Asp Asp Thr Glu Ser Asn Thr Thr Ser Val Asn Leu Pro
 1               5                  10                  15

Thr

<210> SEQ ID NO 15
<211> LENGTH: 18
<212> TYPE: PRT
<213> ORGANISM: Artificial Sequence
<220> FEATURE:
<223> OTHER INFORMATION: Variation

<400> SEQUENCE: 15

Gln Pro Ile Asp Asp Thr Glu Ser Asn Thr Thr Leu Val Asn Val Pro
 1               5                  10                  15

Gly Ala

<210> SEQ ID NO 16
<211> LENGTH: 21
<212> TYPE: PRT
<213> ORGANISM: Artificial Sequence
<220> FEATURE:
<223> OTHER INFORMATION: Variation

<400> SEQUENCE: 16

Gln Pro Ile Asp Asp Thr Glu Ser Asn Thr Thr Ser Val Asn Leu Met
 1               5                  10                  15

Ala Pro Ala Val Ala
            20

<210> SEQ ID NO 17
<211> LENGTH: 25
<212> TYPE: PRT
<213> ORGANISM: Artificial Sequence
<220> FEATURE:
<223> OTHER INFORMATION: Variation
```

```
<400> SEQUENCE: 17

Gln Pro Ile Asp Asp Thr Glu Ser Asn Thr Thr Ser Val Asn Leu Met
1               5                   10                  15

Asp Leu Ala Val Gly Leu Pro Gly Ala
            20                  25

<210> SEQ ID NO 18
<211> LENGTH: 33
<212> TYPE: PRT
<213> ORGANISM: Artificial Sequence
<220> FEATURE:
<223> OTHER INFORMATION: Variation

<400> SEQUENCE: 18

Gln Pro Ile Asp Asp Thr Glu Ser Asn Thr Thr Ser Val Asn Leu Met
1               5                   10                  15

Ala Asp Asp Thr Glu Ser Ile Asn Thr Thr Leu Val Asn Leu Pro Gly
            20                  25                  30

Ala

<210> SEQ ID NO 19
<211> LENGTH: 19
<212> TYPE: PRT
<213> ORGANISM: Artificial Sequence
<220> FEATURE:
<223> OTHER INFORMATION: Variation

<400> SEQUENCE: 19

Gln Pro Ile Asp Asp Thr Glu Ser Ile Asn Thr Thr Leu Val Asn Leu
1               5                   10                  15

Pro Gly Ala

<210> SEQ ID NO 20
<211> LENGTH: 18
<212> TYPE: PRT
<213> ORGANISM: Artificial Sequence
<220> FEATURE:
<223> OTHER INFORMATION: Variation

<400> SEQUENCE: 20

Gln Pro Ile Asp Asp Thr Glu Ser Asn Thr Thr Leu Val Asn Leu Pro
1               5                   10                  15

Gly Ala

<210> SEQ ID NO 21
<211> LENGTH: 35
<212> TYPE: PRT
<213> ORGANISM: Artificial Sequence
<220> FEATURE:
<223> OTHER INFORMATION: Variation

<400> SEQUENCE: 21

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Leu Val Asn
            20                  25                  30

Leu Pro Leu
        35

<210> SEQ ID NO 22
<211> LENGTH: 36
<212> TYPE: PRT
```

```
<213> ORGANISM: Artificial Sequence
<220> FEATURE:
<223> OTHER INFORMATION: Variation

<400> SEQUENCE: 22

Gln Pro Ile Asp Asp Thr Glu Ser Asn Thr Thr Ser Val Asn Leu Met
 1               5                  10                  15

Ala Asp Asp Thr Glu Ser Ile Asn Thr Thr Leu Val Asn Leu Ala Asn
            20                  25                  30

Val Ala Met Ala
         35

<210> SEQ ID NO 23
<211> LENGTH: 20
<212> TYPE: PRT
<213> ORGANISM: Artificial Sequence
<220> FEATURE:
<223> OTHER INFORMATION: Variation

<400> SEQUENCE: 23

Gln Pro Ile Asp Asp Thr Glu Ser Ala Ile Asn Thr Thr Leu Val Asn
 1               5                  10                  15

Leu Pro Gly Ala
         20

<210> SEQ ID NO 24
<211> LENGTH: 21
<212> TYPE: PRT
<213> ORGANISM: Artificial Sequence
<220> FEATURE:
<223> OTHER INFORMATION: Variation

<400> SEQUENCE: 24

Gln Pro Ile Asp Asp Thr Glu Ser Phe Ala Thr Asn Thr Thr Leu Val
 1               5                  10                  15

Asn Leu Pro Gly Ala
         20

<210> SEQ ID NO 25
<211> LENGTH: 36
<212> TYPE: PRT
<213> ORGANISM: Artificial Sequence
<220> FEATURE:
<223> OTHER INFORMATION: Variation

<400> SEQUENCE: 25

Gln Pro Ile Asp Asp Thr Glu Ser Ile Asn Thr Thr Leu Val Asn Leu
 1               5                  10                  15

Met Ala Asp Asp Thr Glu Ser Arg Phe Ala Thr Asn Thr Thr Leu Val
            20                  25                  30

Asn Leu Pro Leu
         35

<210> SEQ ID NO 26
<211> LENGTH: 16
<212> TYPE: PRT
<213> ORGANISM: Artificial Sequence
<220> FEATURE:
<223> OTHER INFORMATION: Variation

<400> SEQUENCE: 26

Arg Phe Ala Thr Asn Thr Thr Leu Asp Val Val Asn Leu Pro Gly Ala
 1               5                  10                  15
```

```
<210> SEQ ID NO 27
<211> LENGTH: 21
<212> TYPE: PRT
<213> ORGANISM: Artificial Sequence
<220> FEATURE:
<223> OTHER INFORMATION: Variation

<400> SEQUENCE: 27

Gln Pro Ile Asp Asp Thr Glu Ser Ala Ala Ile Asn Thr Thr Leu Val
 1               5                  10                  15

Asn Leu Pro Gly Ala
            20

<210> SEQ ID NO 28
<211> LENGTH: 39
<212> TYPE: PRT
<213> ORGANISM: Artificial Sequence
<220> FEATURE:
<223> OTHER INFORMATION: Variation

<400> SEQUENCE: 28

Gln Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Val Asn
            20                  25                  30

Leu Ala Asn Val Ala Met Ala
            35

<210> SEQ ID NO 29
<211> LENGTH: 39
<212> TYPE: PRT
<213> ORGANISM: Artificial Sequence
<220> FEATURE:
<223> OTHER INFORMATION: Variation

<400> SEQUENCE: 29

Gln Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Asp Val
            20                  25                  30

Val Asn Leu Ile Ser Met Ala
            35

<210> SEQ ID NO 30
<211> LENGTH: 39
<212> TYPE: PRT
<213> ORGANISM: Artificial Sequence
<220> FEATURE:
<223> OTHER INFORMATION: Variation

<400> SEQUENCE: 30

Gln Pro Ile Asp Asp Thr Glu Ser Asn Thr Thr Ser Val Asn Leu Met
 1               5                  10                  15

Ala Asn Thr Thr Glu Ser Arg Phe Ala Thr Asn Thr Thr Leu Asp Val
            20                  25                  30

Val Asn Leu Ile Ser Met Ala
            35

<210> SEQ ID NO 31
<211> LENGTH: 43
<212> TYPE: PRT
<213> ORGANISM: Artificial Sequence
<220> FEATURE:
```

```
<223> OTHER INFORMATION: Variation

<400> SEQUENCE: 31

Gln Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Ala Leu
                20                  25                  30

Asp Val Val Asn Leu Ile Ser Met Ala Lys Arg
            35                  40

<210> SEQ ID NO 32
<211> LENGTH: 45
<212> TYPE: PRT
<213> ORGANISM: Artificial Sequence
<220> FEATURE:
<223> OTHER INFORMATION: Variation

<400> SEQUENCE: 32

Gln Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Ala Gly
                20                  25                  30

Gly Leu Asp Val Val Asn Leu Ile Ser Met Ala Lys Arg
            35                  40                  45

<210> SEQ ID NO 33
<211> LENGTH: 43
<212> TYPE: PRT
<213> ORGANISM: Artificial Sequence
<220> FEATURE:
<223> OTHER INFORMATION: Variation

<400> SEQUENCE: 33

Gln Pro Ile Asp Asp Thr Glu Ser Asn Thr Thr Ser Val Asn Leu Met
 1               5                  10                  15

Ala Asp Asp Thr Glu Ser Ala Phe Ala Thr Asn Thr Thr Leu Ala Leu
                20                  25                  30

Asp Val Val Asn Leu Ile Ser Met Ala Lys Arg
            35                  40

<210> SEQ ID NO 34
<211> LENGTH: 43
<212> TYPE: PRT
<213> ORGANISM: Artificial Sequence
<220> FEATURE:
<223> OTHER INFORMATION: Variation

<400> SEQUENCE: 34

Ser Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Ala Leu
                20                  25                  30

Asp Val Val Asn Leu Ile Ser Met Ala Lys Arg
            35                  40

<210> SEQ ID NO 35
<211> LENGTH: 45
<212> TYPE: PRT
<213> ORGANISM: Artificial Sequence
<220> FEATURE:
<223> OTHER INFORMATION: Variation

<400> SEQUENCE: 35
```

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Asn Ser Gly
                20                  25                  30

Gly Leu Asp Val Val Asn Leu Ile Ser Met Ala Lys Arg
            35                  40                  45

<210> SEQ ID NO 36
<211> LENGTH: 45
<212> TYPE: PRT
<213> ORGANISM: Artificial Sequence
<220> FEATURE:
<223> OTHER INFORMATION: Variation

<400> SEQUENCE: 36

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Ser Val Gly
                20                  25                  30

Gly Leu Asp Val Val Asn Leu Ile Ser Met Ala Lys Arg
            35                  40                  45

<210> SEQ ID NO 37
<211> LENGTH: 45
<212> TYPE: PRT
<213> ORGANISM: Artificial Sequence
<220> FEATURE:
<223> OTHER INFORMATION: Variation

<400> SEQUENCE: 37

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Leu Ala Gly
                20                  25                  30

Gly Leu Asp Val Val Gly Leu Ile Ser Met Ala Lys Arg
            35                  40                  45

<210> SEQ ID NO 38
<211> LENGTH: 44
<212> TYPE: PRT
<213> ORGANISM: Artificial Sequence
<220> FEATURE:
<223> OTHER INFORMATION: Variation

<400> SEQUENCE: 38

Gln Pro Asp Asp Thr Glu Ser Asn Thr Thr Ser Val Asn Leu Met Ala
1               5                   10                  15

Asp Asp Thr Glu Ser Ala Phe Ala Thr Asn Thr Thr Ser Val Gly Gly
                20                  25                  30

Leu Asp Val Val Gly Leu Ile Ser Met Ala Lys Arg
            35                  40

<210> SEQ ID NO 39
<211> LENGTH: 45
<212> TYPE: PRT
<213> ORGANISM: Artificial Sequence
<220> FEATURE:
<223> OTHER INFORMATION: Variation

<400> SEQUENCE: 39

Gln Pro Ile Asp Asp Thr Glu Ser Asn Thr Thr Ser Val Asn Leu Met
1               5                   10                  15

```
Ala Asp Asp Thr Glu Ser Ala Phe Ala Thr Asn Thr Leu Ala Gly
            20                  25                  30

Gly Leu Asp Val Val Asn Leu Ile Ser Met Ala Lys Arg
            35                  40              45

<210> SEQ ID NO 40
<211> LENGTH: 45
<212> TYPE: PRT
<213> ORGANISM: Artificial Sequence
<220> FEATURE:
<223> OTHER INFORMATION: Variation

<400> SEQUENCE: 40

Gln Pro Ile Asp Asp Thr Glu Ser Asn Thr Thr Ser Val Asn Leu Met
1               5                   10                  15

Ala Asp Asp Thr Glu Ser Ala Phe Ala Thr Asn Thr Thr Asn Ser Gly
            20                  25                  30

Gly Leu Asp Val Val Asn Leu Ile Ser Met Ala Lys Arg
            35                  40              45

<210> SEQ ID NO 41
<211> LENGTH: 45
<212> TYPE: PRT
<213> ORGANISM: Artificial Sequence
<220> FEATURE:
<223> OTHER INFORMATION: Variation

<400> SEQUENCE: 41

Gln Pro Ile Asp Asp Thr Glu Ser Asn Thr Thr Ser Val Asn Leu Met
1               5                   10                  15

Ala Asp Asp Thr Glu Ser Ala Phe Ala Thr Asn Thr Thr Leu Ala Gly
            20                  25                  30

Gly Leu Asp Val Val Gly Leu Ile Ser Met Ala Lys Arg
            35                  40              45

<210> SEQ ID NO 42
<211> LENGTH: 18
<212> TYPE: PRT
<213> ORGANISM: Artificial Sequence
<220> FEATURE:
<223> OTHER INFORMATION: Variation

<400> SEQUENCE: 42

Glu Glu Ala Glu Ala Glu Pro Ala Glu Lys Ala Glu Lys Thr Arg Ala
1               5                   10                  15

Pro Arg

<210> SEQ ID NO 43
<211> LENGTH: 12
<212> TYPE: PRT
<213> ORGANISM: Artificial Sequence
<220> FEATURE:
<223> OTHER INFORMATION: Variation

<400> SEQUENCE: 43

Glu Glu Ala Glu Ala Glu Pro Lys Ala Thr Pro Arg
1               5                   10

<210> SEQ ID NO 44
<211> LENGTH: 10
<212> TYPE: PRT
<213> ORGANISM: Artificial Sequence
<220> FEATURE:
```

<223> OTHER INFORMATION: Variation

<400> SEQUENCE: 44

Glu Glu Ala Glu Ala Glu Ala Glu Pro Arg
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: Variation

<400> SEQUENCE: 45

Glu Glu Ala Glu Ala Glu Ala Glu Pro Lys
 1               5                  10

<210> SEQ ID NO 46
<211> LENGTH: 9
<212> TYPE: PRT
<213> ORGANISM: Artificial Sequence
<220> FEATURE:
<223> OTHER INFORMATION: Variation

<400> SEQUENCE: 46

Glu Glu Ala Glu Ala Glu Ala Glu Arg
 1               5

<210> SEQ ID NO 47
<211> LENGTH: 12
<212> TYPE: PRT
<213> ORGANISM: Artificial Sequence
<220> FEATURE:
<223> OTHER INFORMATION: Variation

<400> SEQUENCE: 47

Glu Glu Ala Glu Ala Glu Ala Asp Ala Gly Glu Lys
 1               5                  10

<210> SEQ ID NO 48
<211> LENGTH: 12
<212> TYPE: PRT
<213> ORGANISM: Artificial Sequence
<220> FEATURE:
<223> OTHER INFORMATION: Variation

<400> SEQUENCE: 48

Glu Glu Ala Glu Ala Glu Ala Pro Leu Ile Thr Lys
 1               5                  10

<210> SEQ ID NO 49
<211> LENGTH: 8
<212> TYPE: PRT
<213> ORGANISM: Artificial Sequence
<220> FEATURE:
<223> OTHER INFORMATION: Variation

<400> SEQUENCE: 49

Glu Glu Ala Glu Ala Glu Ala Arg
 1               5

<210> SEQ ID NO 50
<211> LENGTH: 11
<212> TYPE: PRT
<213> ORGANISM: Artificial Sequence
<220> FEATURE:
<223> OTHER INFORMATION: Variation

```
<400> SEQUENCE: 50

Glu Glu Ala Glu Ala Glu Glu Asp Gly Ala Lys
 1               5                  10

<210> SEQ ID NO 51
<211> LENGTH: 7
<212> TYPE: PRT
<213> ORGANISM: Artificial Sequence
<220> FEATURE:
<223> OTHER INFORMATION: Variation

<400> SEQUENCE: 51

Glu Glu Ala Glu Ala Pro Lys
 1               5

<210> SEQ ID NO 52
<211> LENGTH: 5
<212> TYPE: PRT
<213> ORGANISM: Artificial Sequence
<220> FEATURE:
<223> OTHER INFORMATION: Variation

<400> SEQUENCE: 52

Glu Glu Ala Pro Lys
 1               5

<210> SEQ ID NO 53
<211> LENGTH: 10
<212> TYPE: PRT
<213> ORGANISM: Artificial Sequence
<220> FEATURE:
<223> OTHER INFORMATION: Variation

<400> SEQUENCE: 53

Asp Asp Ala Asp Ala Asp Ala Asp Pro Arg
 1               5                  10

<210> SEQ ID NO 54
<211> LENGTH: 6
<212> TYPE: PRT
<213> ORGANISM: Artificial Sequence
<220> FEATURE:
<223> OTHER INFORMATION: Variation

<400> SEQUENCE: 54

Glu Glu Glu Glu Pro Lys
 1               5

<210> SEQ ID NO 55
<211> LENGTH: 5
<212> TYPE: PRT
<213> ORGANISM: Artificial Sequence
<220> FEATURE:
<223> OTHER INFORMATION: Variation

<400> SEQUENCE: 55

Glu Glu Glu Pro Lys
 1               5

<210> SEQ ID NO 56
<211> LENGTH: 6
<212> TYPE: PRT
<213> ORGANISM: Artificial Sequence
<220> FEATURE:
<223> OTHER INFORMATION: Variation
```

```
<400> SEQUENCE: 56

Asp Asp Asp Asp Asp Lys
  1               5

<210> SEQ ID NO 57
<211> LENGTH: 4
<212> TYPE: PRT
<213> ORGANISM: Artificial Sequence
<220> FEATURE:
<223> OTHER INFORMATION: Variation

<400> SEQUENCE: 57

Glu Glu Pro Lys
  1

<210> SEQ ID NO 58
<211> LENGTH: 6
<212> TYPE: DNA
<213> ORGANISM: Artificial Sequence
<220> FEATURE:
<223> OTHER INFORMATION: Primer

<400> SEQUENCE: 58 ccatgg                                                                 6

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
aatttatttt acataacact ag                                              22

<210> SEQ ID NO 60
<211> LENGTH: 6
<212> TYPE: DNA
<213> ORGANISM: Artificial Sequence
<220> FEATURE:
<223> OTHER INFORMATION: Primer

<400> SEQUENCE: 60 tctaga                                                                 6

<210> SEQ ID NO 61
<211> LENGTH: 5
<212> TYPE: PRT
<213> ORGANISM: Artificial Sequence
<220> FEATURE:
<223> OTHER INFORMATION: Variation

<400> SEQUENCE: 61

Asp Lys Ala Ala Lys
  1               5

<210> SEQ ID NO 62
<211> LENGTH: 64
<212> TYPE: DNA
<213> ORGANISM: Artificial Sequence
<220> FEATURE:
<223> OTHER INFORMATION: Primer

<400> SEQUENCE: 62
ggggtatcca tggctaagag agaagaagct gaagctgaag ctaccaaagt tcgttaacca     60
``` acac                                                              64

<210> SEQ ID NO 63
<211> LENGTH: 21
<212> TYPE: PRT
<213> ORGANISM: Artificial Sequence
<220> FEATURE:
<223> OTHER INFORMATION: Variation
<221> NAME/KEY: VARIANT
<222> LOCATION: (1)...(21)
<223> OTHER INFORMATION: Xaa = any amino acid

<400> SEQUENCE: 63

Gly Leu Ser Met Ala Lys Arg Glu Glu Ala Glu Ala Glu Ala Xaa Lys
 1               5                  10                  15

Phe Val Asn Gln His
            20

<210> SEQ ID NO 64
<211> LENGTH: 9
<212> TYPE: PRT
<213> ORGANISM: Arificial Sequence
<220> FEATURE:
<223> OTHER INFORMATION: Variation
<223> OTHER INFORMATION: Xaa is any amino acid
<221> NAME/KEY: VARIANT
<222> LOCATION: (1)...(9)
<223> OTHER INFORMATION: Xaa = Any Amino Acid

<400> SEQUENCE: 64

Glu Glu Ala Glu Ala Glu Ala Xaa Lys
 1               5

<210> SEQ ID NO 65
<211> LENGTH: 67
<212> TYPE: DNA
<213> ORGANISM: Artificial Sequence
<220> FEATURE:
<223> OTHER INFORMATION: Primer

<400> SEQUENCE: 65
ggggtatcca tggctaagag agaagaagct gaagctgaag ctgcagacaa agttcgttaa    60
ccaacac                                                              67

<210> SEQ ID NO 66
<211> LENGTH: 21
<212> TYPE: PRT
<213> ORGANISM: Artificial Sequence
<220> FEATURE:
<223> OTHER INFORMATION: Variation
<223> OTHER INFORMATION: Xaa is any amino acid
<221> NAME/KEY: VARIANT
<222> LOCATION: (1)...(21)
<223> OTHER INFORMATION: Xaa = Any Amino Acid

<400> SEQUENCE: 66

Gly Leu Ser Met Ala Lys Arg Glu Glu Ala Glu Ala Glu Ala Xaa Lys
 1               5                  10                  15

Phe Val Asn Gln His
            20

<210> SEQ ID NO 67
<211> LENGTH: 62
<212> TYPE: DNA
<213> ORGANISM: Artificial Sequence
<220> FEATURE:
<223> OTHER INFORMATION: Primer

<400> SEQUENCE: 67
ggggtatcca tggctaagag agaagaagct gaagctgaag gacaaagttc gttaaccaac    60
ac                                                                  62

<210> SEQ ID NO 68
<211> LENGTH: 20
<212> TYPE: PRT
<213> ORGANISM: Artificial Sequence
<220> FEATURE:
<223> OTHER INFORMATION: Variation
<223> OTHER INFORMATION: Xaa is any amino acid
<221> NAME/KEY: VARIANT
<222> LOCATION: (1)...(20)
<223> OTHER INFORMATION: Xaa = Any Amino Acid

<400> SEQUENCE: 68

Gly Leu Ser Met Ala Lys Arg Glu Glu Ala Glu Ala Glu Xaa Lys Phe
 1               5                  10                  15

Val Asn Gln His
            20

<210> SEQ ID NO 69
<211> LENGTH: 8
<212> TYPE: PRT
<213> ORGANISM: Artificial Sequence
<220> FEATURE:
<223> OTHER INFORMATION: Variation
<223> OTHER INFORMATION: Xaa is any amino acid
<221> NAME/KEY: VARIANT
<222> LOCATION: (1)...(8)
<223> OTHER INFORMATION: Xaa = Any Amino Acid

<400> SEQUENCE: 69

Glu Glu Ala Glu Ala Glu Xaa Lys
 1               5

<210> SEQ ID NO 70
<211> LENGTH: 72
<212> TYPE: DNA
<213> ORGANISM: Artificial Sequence
<220> FEATURE:
<223> OTHER INFORMATION: Primer

<400> SEQUENCE: 70
aacgttgcca tggctccagc tccagctaag agagaagaag ctgaagctga agctgaaaga    60
catgctgaag gt                                                       72

<210> SEQ ID NO 71
<211> LENGTH: 24
<212> TYPE: PRT
<213> ORGANISM: Artificial Sequence
<220> FEATURE:
<223> OTHER INFORMATION: Variation

<400> SEQUENCE: 71

Asn Val Ala Met Ala Pro Ala Val Ala Lys Arg Glu Glu Ala Glu Ala
 1               5                  10                  15

Glu Ala Glu Arg His Ala Glu Gly
            20

<210> SEQ ID NO 72
<211> LENGTH: 9
<212> TYPE: PRT
<213> ORGANISM: Artificial Sequence

```
<220> FEATURE:
<223> OTHER INFORMATION: Variation

<400> SEQUENCE: 72

Glu Glu Ala Glu Ala Glu Ala Pro Lys
 1               5

<210> SEQ ID NO 73
<211> LENGTH: 9
<212> TYPE: PRT
<213> ORGANISM: Artificial Sequence
<220> FEATURE:
<223> OTHER INFORMATION: Variation

<400> SEQUENCE: 73

Glu Glu Ala Glu Ala Glu Ala Thr Lys
 1               5

<210> SEQ ID NO 74
<211> LENGTH: 9
<212> TYPE: PRT
<213> ORGANISM: Artificial Sequence
<220> FEATURE:
<223> OTHER INFORMATION: Variation

<400> SEQUENCE: 74

Glu Glu Ala Glu Ala Glu Ala Glu Lys
 1               5

<210> SEQ ID NO 75
<211> LENGTH: 9
<212> TYPE: PRT
<213> ORGANISM: Artificial Sequence
<220> FEATURE:
<223> OTHER INFORMATION: Variation

<400> SEQUENCE: 75

Glu Glu Ala Glu Ala Glu Ala Asp Lys
 1               5

<210> SEQ ID NO 76
<211> LENGTH: 9
<212> TYPE: PRT
<213> ORGANISM: Artificial Sequence
<220> FEATURE:
<223> OTHER INFORMATION: Variation

<400> SEQUENCE: 76

Glu Glu Ala Glu Ala Glu Ala Gly Lys
 1               5

<210> SEQ ID NO 77
<211> LENGTH: 8
<212> TYPE: PRT
<213> ORGANISM: Artificial Sequence
<220> FEATURE:
<223> OTHER INFORMATION: Variation

<400> SEQUENCE: 77

Glu Glu Ala Glu Ala Glu Ala Lys
 1               5

<210> SEQ ID NO 78
<211> LENGTH: 8
<212> TYPE: PRT
<213> ORGANISM: Artificial Sequence
<220> FEATURE:
```

<223> OTHER INFORMATION: Variation

<400> SEQUENCE: 78

Glu Glu Ala Glu Ala Glu Glu Lys
 1               5

<210> SEQ ID NO 79
<211> LENGTH: 5
<212> TYPE: PRT
<213> ORGANISM: Artificial Sequence
<220> FEATURE:
<223> OTHER INFORMATION: Variation

<400> SEQUENCE: 79

Pro Lys Ala Ala Arg
 1               5

<210> SEQ ID NO 80
<211> LENGTH: 74
<212> TYPE: DNA
<213> ORGANISM: Artificial Sequence
<220> FEATURE:
<223> OTHER INFORMATION: Primer

<400> SEQUENCE: 80
ggggtatcca tggctaagag agacgacgct gacgctgacg ctgacccaag attcgttaac     60
caacacttgt gcgg                                                       74

<210> SEQ ID NO 81
<211> LENGTH: 24
<212> TYPE: PRT
<213> ORGANISM: Artificial Sequence
<220> FEATURE:
<223> OTHER INFORMATION: Variation

<400> SEQUENCE: 81

Gly Leu Ser Met Ala Lys Arg Asp Asp Ala Asp Ala Asp Ala Asp Pro
 1               5                  10                  15

Arg Phe Val Asn Gln His Leu Cys
            20

<210> SEQ ID NO 82
<211> LENGTH: 13
<212> TYPE: PRT
<213> ORGANISM: Artificial Sequence
<220> FEATURE:
<223> OTHER INFORMATION: Variation

<400> SEQUENCE: 82

Glu Glu Ala Glu Ala Glu Ala Glu Pro Lys Ala Thr Arg
 1               5                  10

<210> SEQ ID NO 83
<211> LENGTH: 83
<212> TYPE: DNA
<213> ORGANISM: Artificial Sequence
<220> FEATURE:
<223> OTHER INFORMATION: Primer

<400> SEQUENCE: 83
ggggtatcca tggctaagag agaagaagct gaagctgaag ctgaaccaaa ggctacaaga     60
ttcgttaacc aacacttgtg cgg                                             83

<210> SEQ ID NO 84

```
<211> LENGTH: 27
<212> TYPE: PRT
<213> ORGANISM: Artificial Sequence
<220> FEATURE:
<223> OTHER INFORMATION: Variation

<400> SEQUENCE: 84

Gly Leu Ser Met Ala Lys Arg Glu Glu Ala Glu Ala Glu Ala Glu Pro
 1               5                  10                  15

Lys Ala Thr Arg Phe Val Asn Gln His Leu Cys
                20                  25

<210> SEQ ID NO 85
<211> LENGTH: 39
<212> TYPE: DNA
<213> ORGANISM: Artificial Sequence
<220> FEATURE:
<223> OTHER INFORMATION: Primer

<400> SEQUENCE: 85
gaagaagaag aagaagaacc aaagttcgtt aaccaacac                    39

<210> SEQ ID NO 86
<211> LENGTH: 13
<212> TYPE: PRT
<213> ORGANISM: Artificial Sequence
<220> FEATURE:
<223> OTHER INFORMATION: Variation

<400> SEQUENCE: 86

Glu Glu Glu Glu Glu Glu Pro Lys Phe Val Asn Gln His
 1               5                  10

<210> SEQ ID NO 87
<211> LENGTH: 36
<212> TYPE: DNA
<213> ORGANISM: Artificial Sequence
<220> FEATURE:
<223> OTHER INFORMATION: Primer

<400> SEQUENCE: 87
gttgttaact tgatctccat ggctaagaga gaagaa                       36

<210> SEQ ID NO 88
<211> LENGTH: 12
<212> TYPE: PRT
<213> ORGANISM: Artificial Sequence
<220> FEATURE:
<223> OTHER INFORMATION: Variation

<400> SEQUENCE: 88

Val Val Asn Leu Ile Ser Met Ala Lys Arg Glu Glu
 1               5                  10

<210> SEQ ID NO 89
<211> LENGTH: 41
<212> TYPE: DNA
<213> ORGANISM: Artificial Sequence
<220> FEATURE:
<223> OTHER INFORMATION: Primer

<400> SEQUENCE: 89
tctccatggc taagagagaa gaagctgaac caaagttcgt t                 41

<210> SEQ ID NO 90
<211> LENGTH: 22
```

```
<212> TYPE: DNA
<213> ORGANISM: Artificial Sequence
<220> FEATURE:
<223> OTHER INFORMATION: Primer

<400> SEQUENCE: 90 aatttattt acataacact ag                                        22

<210> SEQ ID NO 91
<211> LENGTH: 46
<212> TYPE: DNA
<213> ORGANISM: Artificial Sequence
<220> FEATURE:
<223> OTHER INFORMATION: Primer

<400> SEQUENCE: 91
gatctccatg gctaagagag aagaaytgaa ccaaagttcg ttaacc             46

<210> SEQ ID NO 92
<211> LENGTH: 27
<212> TYPE: DNA
<213> ORGANISM: Artifiicial Sequence

<400> SEQUENCE: 92
ttaatcttag tttctagagc ctgcggg                                  27

<210> SEQ ID NO 93
<211> LENGTH: 27
<212> TYPE: DNA
<213> ORGANISM: Artificial Sequence
<220> FEATURE:
<223> OTHER INFORMATION: Primer

<400> SEQUENCE: 93
ttaatcttag tttctagagc ctgcggg                                  27
```

N-TERMINALLY EXTENDED PROTEINS EXPRESSED IN YEAST

CROSS-REFERENCE TO RELATED APPLICATIONS

This application is a continuation-in-part of U.S. Ser. No. 08/991,801, filed Dec. 16, 1997, now abandoned, which application is specifically incorporated by reference, which claims priority under 35 USC 119 to Danish application 1482/96, filed Dec. 20, 1996. This application is also a continuation-in-part of U.S. Ser. No. 08/766,011, filed Dec. 13, 1996, now abandoned, which application is specifically incorporated by reference, which claims priority under 35 USC 119 to Danish application 1449/95, filed Dec. 20, 1995, and is a continuation-in-part of U.S. Ser. No. 08/490,689, filed Jun. 15, 1995, now abandoned, which is a continuation of U.S. Ser. No. 08/286,059, filed Aug. 4, 1994, now abandoned, which application is specifically incorporated by reference, which claims priority under 35 USC 119 to Danish application 0712/94, filed Jun. 17, 1994.

FIELD OF INVENTION

The present invention relates to polypeptides produced in yeast, a DNA construct comprising a DNA sequence encoding such polypeptides, vectors carrying such DNA fragments and yeast cells transformed with the vectors, as well as a process of producing heterologous proteins in yeast.

BACKGROUND OF THE INVENTION

Yeast organisms produce a number of proteins synthesized intracellularly, but having a function outside the cell. Such extracelluar proteins are referred to as secreted proteins. These secreted proteins are expressed initially inside the cell in a precursor or a pre-form containing a pre-peptide sequence ensuring effective direction of the expressed product across the membrane of the endoplasmic reticulum (ER). The pre-peptide, normally named a signal peptide, is generally cleaved off from the desired product during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer et al. (1987) Ann. Rev. Biochem. 56:829–852).

Several approaches have been suggested for the expression and secretion in yeast of proteins heterologous to yeast. European publication 088632A describes a process by which proteins heterologous to yeast are expressed, processed and secreted by transforming a yeast organism with an expression vector harbouring DNA encoding the desired protein and a signal peptide, preparing a culture of the transformed organism, growing the culture and recovering the protein from the culture medium. The signal peptide may be the desired protein's heterologous signal peptide, or a hybrid of a homologous and a heterologous signal peptide.

A problem encountered with the use of signal peptides heterologous to yeast may be that the heterologous signal peptide does not ensure efficient translocation and/or cleavage after the signal peptide.

The *Saccharomyces cerevisiae* MFα1 (α-factor) is synthesized as a pre-pro form of 165 amino acids comprising a 19 amino acids long signal- or pre-peptide followed by a 64 amino acids long "leader" or pro-peptide, (Kurjan et al. (1982) Cell 30:933–943). Use of signal/leader peptides homologous to yeast is described in U.S. Pat. No. 4,546,082; EP publications 0116201A, 0123294A, 0123544A, 0163529A, 0123289A, EP No. 0100561B, and PCT Publication WO 95/02059.

In EP 0123289A utilization of the *S. cerevisiae* α-factor precursor is described whereas EP 0100561 describes the utilization of the *S. cerevisiae* PHO5 signal and WO 95/02059 describes the utilization of YAP3 signal peptide for secretion of foreign proteins.

U.S. Pat. No. 4,546,082 and European Publication Nos. 0016201A, 0123294A, 0123544A and 0163529A describe processes by which the α-factor signal-leader from *S. cerevisiae* (MFα1 or MFα2) is utilized in the secretion process of expressed heterologous proteins in yeast. Secretion and processing of the desired protein was demonstrated by fusing a DNA sequence encoding the *S. cerevisiae* MFα1 signal/leader peptide at the 5' end of the gene for the desired protein.

EP 0206783 discloses a system for the secretion of polypeptides from *S. cerevisiae* whereby the α-factor signal/leader sequence has been truncated to eliminate the four α-factor peptides present on the native sequence so as to leave the signal/leader peptide itself fused to a heterologous polypeptide via the α-factor processing site Lys-Arg-Glu-Ala-Glu-Ala (SEQ ID NO:93). It is indicated that this construction leads to an efficient process for production of smaller peptides (less than 50 amino acids). For the secretion and processing of larger polypeptides, the native α-factor leader sequence has been truncated to leave one or two α-factor peptides between the leader peptide and the polypeptide.

A number of secreted proteins are routed so that the precursor is exposed to a proteolytic processing system which can cleave the peptide bond at the carboxy end of two consecutive basic amino acids. This enzymatic activity is in *S. cerevisiae* encoded by the KEX 2 gene (Julius et al. (1984) Cell 37:1075). Processing of the product by the KEX 2 protease is needed for the secretion of active *S. cerevisiae* mating factor α1 (MFα1 or α-factor) but is not involved in the secretion of active *S. cerevisiae* mating factor a.

Secretion and correct processing of a polypeptide intended to be secreted is obtained in some cases when culturing a yeast organism which is transformed with a vector constructed as indicated in the references given above. In many cases, however, the level of secretion is very low or there is no secretion, or the proteolytic processing may be incorrect or incomplete. As described in WO 90/10075, this is believed to be ascribable, to some extent, to an insufficient exposure of the processing site present between the C-terminal end of the leader peptide and the N-terminal end of the heterologous protein so as to render it inaccessible, or less accessible, to proteolytic cleavage, for example, by the KEX 2 protease.

WO 90/10075 describes a yeast expression system with improved processing of a heterologous polypeptide obtained by providing certain modifications near the processing site at the C-terminal end of the leader peptide and/or the N-terminal end of a heterologous polypeptide fused to the leader peptide.

SUMMARY OF THE INVENTION

The present invention describes modifications of the N-terminal end of the heterologous polypeptide designed as extensions which can be cleaved off either by naturally occurring yeast proteases before purification from the culture media or by in vitro proteolysis during or subsequently to purification of the product from the culture media.

In one aspect, the present invention is drawn to a DNA construct encoding a polypeptide having the structure:

signal peptide-leader peptide-$X^1$-$X^2$-$X^3$-$X^4$$X^5$-$X^6$-$X^7$-heterologous protein wherein $X^1$ is Lys or Arg;

$X^2$ is Lys or Arg, $X^1$ and $X^2$ together defining a yeast processing site;

$X^3$ is Glu or Asp;

$X^4$ is a sequence of amino acids with the following structure (A-B)$_n$ wherein A is Glu or Asp, B is Ala, Val, Leu or Pro, and n is 0 or an integer from 1 to 5, and when n≧2 each A and B is the same or different from the other A(s) and B(s); or $X^4$ is a sequence of amino acids with the following structure (C)$_m$ wherein C is Glu or Asp, and m is 0 or an integer from 1 to 5;

$X^5$ is a peptide bond or is one or more amino acids which may be the same or different;

$X^6$ is a peptide bond or an amino acid residue selected from the group consisting of Pro, Asp, Thr, Glu, Ala and Gly; and $X^7$ is Lys or Arg.

A specific embodiment of the present invention is drawn to a DNA construct encoding a polypeptide having the structure:

signal peptide-leader peptide-$X^1$-$X^2$-$X^3$-$X^4$-$X^5$-$X^6$-$X^7$-heterologous protein wherein $X^3$-$X^4$-$X^5$-$X^6$-$X^7$ are the sequence Glu Glu Ala Glu Pro Lys (SEQ ID NO: 1).

The sequence Glu Glu Ala Glu Pro Lys (SEQ ID NO: 1) forms an extension at the N-terminal of the heterologous polypeptide. This extension not only increases the fermentation yield but is protected against dipeptidyl aminopeptidase (DPAP A) processing, resulting in a homogenous N-terminal of the polypeptide. The extension is constructed in such a way that it is resistant to proteolytic cleavage during fermentation so that the N-terminally extended heterologous protein product can be purified from the culture media for subsequent in vitro maturation, e.g. by trypsin or *Achromobacter lyticus* protease I. The desired in vitro removal of the N-terminal extension of SEQ ID NO:1 is readily achieved by either trypsin or *Achromobacter lyticus* protease I, presumably due to flexibility of the N-terminal extension peptide resulting in an improved yield of the matured heterologous protein.

Another specific embodiment of the present invention is drawn to a DNA construct encoding a polypeptide having the structure:

signal peptide-leader peptide-$X^1$-$X^2$-$X^3$-$X^4$-$X^5$-$X^6$-$X^7$-heterologous protein wherein $X^3$-$X^4$-$X^5$-$X^6$-$X^7$ are the sequence Glu Glu Gly Glu Pro Lys (SEQ ID NO:2).

The sequence Glu Glu Gly Glu Pro Lys (SEQ ID NO:2) forms an extension at the N-terminal of the heterologous polypeptide. Without being bound by any specific theory, it is surprising shown that the location of a glycine (G) in the N-terminal extension compared to the repeated Glu Ala of the α-factor leader results in improved heterologous protein yield which may reflect an improved translocation and/or secretion, since glycine with only a hydrogen atom as a side chain can adopt a much wider range of conformations than other amino acid residues, thus allowing unusual main chain conformations, and a possible more unstable precursor polypeptide and secretion process.

The term "signal peptide" is understood to mean a pre-peptide which is present as an N-terminal sequence on the precursor form of an extracellular protein expressed in yeast. The function of the signal peptide is to allow the heterologous protein to be secreted to enter the endoplasmic reticulum. The signal peptide is normally cleaved off in the course of this process. The signal peptide may be heterologous or homologous to the yeast organism producing the protein. A preferred signal peptide in this invention is yeast aspartic protease 3 (YAP3) signal peptide or any functional analogue thereof. YAP 3 has been cloned and characterised by Egel-Mitani et al. (1990) YEAST 6:127–137.

The term "leader peptide" means a polypeptide sequence whose function is to allow the heterologous protein to be secreted to be directed from the endoplasmic reticulum to the Golgi apparatus and further to a secretory vesicle for secretion into the medium. Preferably the leader peptide used in the present invention is selected from the following group of leader peptides Gln Pro Ile Asp Glu Asp Asn Asp Thr Ser Val Asn Leu Pro Ala (SEQ ID NO:3);

Gln Pro Ile Asp Asp Glu Asn Thr Thr Ser Val Asn Leu Pro Ala (SEQ ID NO:4);

Gln Pro Ile Asp Asp Glu Ser Asn Thr Thr Ser Val Asn Leu Pro Ala(SEQ ID NO:5);

Gln Pro Ile Asp Asp Glu Asn Thr Thr Ser Val Asn Leu Pro Val (SEQ ID NO:6);

Gln Pro Ile Asp Asp Thr Glu Asn Thr Thr Ser Val Asn Leu Pro Ala (SEQ ID NO:7);

Gln Pro Ile Asp Asp Thr Glu Ser Asn Thr Thr Ser Val Asn Leu Pro Ala (SEQ ID NO:8);

Gln Pro Ile Asp Asp Glu Asn Thr Thr Ser Val Asn Leu Met Ala (SEQ ID NO:9);

Gln Pro Ile Asp Asp Thr Glu Ser Asn Thr Thr Ser Val Asn Leu Pro Gly Ala (SEQ ID NO:10);

Gln Pro Ile Asp Asp Thr Glu Ser Asn Thr Thr Ser Val Asn Leu Met Ala (SEQ ID NO:11);

Gln Pro Ile Asp Asp Thr Glu Ser Asn Thr Thr Ser Val Asn Val Pro Thr (SEQ ID NO:12;

Gln Pro Ile Asp Asp Thr Glu Ser Asn Thr Thr Leu Val Asn Val Pro Thr (SEQ ID NO:13;

Gln Pro Ile Asp Asp Thr Glu Ser Asn Thr Thr Ser Val Asn Leu Pro Thr (SEQ ID NO:14);

Gln Pro Ile Asp Asp Thr Glu Ser Asn Thr Thr Leu Val Asn Val Pro Gly Ala (SEQ ID NO:15);

Gln Pro Ile Asp Asp Thr Glu Ser Asn Thr Thr Ser Val Asn Leu Met Ala Pro Ala Val Ala (SEQ ID NO:16);

Gln Pro Ile Asp Asp Thr Glu Ser Asn Thr Thr Ser Val Asn Leu Met Asp Leu Ala Val Gly Leu Pro Gly Ala (SEQ ID NO:17);

Gln Pro Ile Asp Asp Thr Glu Ser Asn Thr Thr Ser Val Asn Leu Met Ala Asp Asp Thr Glu Ser Ile Asn Thr Thr Leu Val Asn Leu Pro Gly Ala (SEQ ID NO:18);

Gln Pro Ile Asp Asp Thr Glu Ser Ile Asn Thr Thr Leu Val Asn Leu Pro Gly Ala (SEQ ID NO:19);

Gln Pro Ile Asp Asp Thr Glu Ser Asn Thr Thr Leu Val Asn Leu Pro Gly Ala (SEQ ID NO:20);

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Val Asn Leu Pro Leu (SEQ ID NO:21);

Gln Pro Ile Asp Asp Thr Glu Ser Asn Thr Thr Ser Val Asn Leu Met Ala Asp Asp Thr Glu Ser Ile Asn Thr Thr Leu Val Asn Leu Ala Asn Val Ala Met Ala (SEQ ID NO:22);

Gln Pro Ile Asp Asp Thr Glu Ser Ala Ile Asn Thr Thr Leu Val Asn Leu Pro Gly Ala (SEQ ID NO:23);

Gln Pro Ile Asp Asp Thr Glu Ser Phe Ala Thr Asn Thr Thr Leu Val Asn Leu Pro Gly Ala (SEQ ID NO:24);

Gln Pro Ile Asp Asp Thr Glu Ser Ile Asn Thr Thr Leu Val Asn Leu Met Ala Asp Asp Thr Glu Ser Arg Phe Ala Thr Asn Thr Thr Leu Val Asn Leu Pro Leu (SEQ ID NO:25);

Gln Pro Ile Asp Asp Thr Glu Ser Ile Asn Thr Thr Leu Val Asn Leu Met Ala Asp Asp Thr Glu Ser Arg Phe Ala Thr Asn Thr Thr Leu Asp Val Val Asn Leu Pro Gly Ala (SEQ ID NO:26);

Gln Pro Ile Asp Asp Thr Glu Ser Ala Ala Ile Asn Thr Thr Leu Val Asn Leu Pro Gly Ala (SEQ ID NO:27);

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Val Asn Leu Ala Asn Val Ala Met Ala (SEQ ID NO:28);

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Asp Val Val Asn Leu Ile Ser Met Ala (SEQ ID NO:29);

Gln Pro Ile Asp Asp Thr Glu Ser Asn Thr Thr Ser Val Asn Leu Met Ala Asn Thr Thr Glu Ser Arg Phe Ala Thr Asn Thr Thr Leu Asp Val Val Asn Leu Ile Ser Met Ala (SEQ ID NO:30);

identified in PCT/DK95/00249 and all C-terminally followed by a Lys-Arg sequence and any functional analogue thereof, and more preferably the leader peptide has an amino acid sequence of 43 or more amino acids, such as the leader peptide (LA19):

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Ala Leu Asp Val Val Asn Leu Ile Ser Met Ala Lys Arg (SEQ ID NO:31);

identified in PCT/DK95/00249 and which includes the C-terminal Lys-Arg processing site, or any functional analogue thereof. In the DNA construct of the present invention the leader peptide preferably contains an endopeptidase processing site at the C-terminal end, such as a Lys-Arg sequence.

Even more preferred leader peptides encoded by the DNA constructs of the invention are:

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Ala Gly Gly Leu Asp Val Val Asn Leu Ile Ser Met Ala Lys Arg (SEQ ID NO:32),

Gln Pro Ile Asp Asp Thr Glu Ser Asn Thr Thr Ser Val Asn Leu Met Ala Asp Asp Thr Glu Ser Ala Phe Ala Thr Asn Thr Thr Leu Ala Leu Asp Val Val Asn Leu Ile Ser Met Ala Lys Arg (SEQ ID NO:33),

Ser Pro Ile Asp Asp Thr Glu Ser Asn Thr Thr Ser Val Asn Leu Met Ala Asp Asp Thr Glu Ser Arg Phe Ala Thr Asn Thr Thr Leu Ala Leu Asp Val Val Asn Leu Ile Ser Met Ala Lys Arg (SEQ ID NO:34),

Gln Pro Ile Asp Asp Thr Glu Ser Asn Thr Thr Ser Val Asn Leu Met Ala Asp Asp Thr Glu Ser Arg Phe Ala Thr Asn Thr Thr Asn Ser Gly Gly Leu Asp Val Val Asn Leu Ile Ser Met Ala Lys Arg (SEQ ID NO:35),

Gln Pro Ile Asp Asp Thr Glu Ser Asn Thr Thr Ser Val Asn Leu Met Ala Asp Asp Thr Glu Ser Arg Phe Ala Thr Asn Thr Thr Ser Val Gly Gly Leu Asp Val Val Asn Leu Ile Ser Met Ala Lys Arg (SEQ ID NO:36),

Gln Pro Ile Asp Asp Thr Glu Ser Asn Thr Thr Ser Val Asn Leu Met Ala Asp Asp Thr Glu Ser Arg Phe Ala Thr Asn Thr Thr Leu Ala Gly Gly Leu Asp Val Val Gly Leu Ile Ser Met Ala Lys Arg (SEQ ID NO:37),

Gln Pro Asp Asp Thr Glu Ser Asn Thr Thr Ser Val Asn Leu Met Ala Asp Asp Thr Glu Ser Ala Phe Ala Thr Asn Thr Thr Ser Val Gly Gly Leu Asp Val Val Gly Leu Ile Ser Met Ala Lys Arg (SEQ ID NO:38),

Gln Pro Ile Asp Asp Thr Glu Ser Asn Thr Thr Ser Val Asn Leu Met Ala Asp Asp Thr Glu Ser Ala Phe Ala Thr AsnThr Thr Leu Ala Gly Gly Leu Asp Val Val Asn Leu Ile Ser Met Ala Lys Arg (SEQ ID NO:39),

Gln Pro Ile Asp Asp Thr Glu Ser Asn Thr Thr Ser Val Asn Leu Met Ala Asp Asp Thr Glu Ser Ala Phe Ala Thr Asn Thr Thr Asn Ser Gly Gly Leu Asp Val Val Asn Leu Ile Ser Met Ala Lys Arg (SEQ ID NO:40),

Gln Pro Ile Asp Asp Thr Glu Ser Asn Thr Thr Ser Val Asn Leu Met Ala Asp Asp Thr Glu Ser Ala Phe Ala Thr Asn Thr Thr Leu Ala Gly Gly Leu Asp Val Val Gly Leu Ile Ser Met Ala Lys Arg (SEQ ID NO:41).

The term "heterologous protein" means a protein or polypeptide which is not produced by the host yeast organism in nature.

In a still further aspect, the invention relates to a process for producing a heterologous protein in yeast, comprising cultivating the transformed yeast strain in a suitable medium to obtain expression and secretion of the heterologous protein, after which the protein is isolated from the medium.

The invention further relates to a recombinant expression vector which is capable of replicating in a eucaryotic cell, preferably a yeast cell, and which carries a DNA construct of the invention. Preferably, the DNA construct comprises a synthetic leader peptide, preferably the LA19 leader peptide. Besides, the invention relates to the DNA construct described in FIG. 2 herein. The invention also relates to a eucaryotic cell, preferably a yeast cell, which is capable of expressing a heterologous protein and which is transformed with a vector of the invention.

BRIEF DESCRIPTION OF THE DRAWINGS

FIGS. 2–3 shows the DNA sequence in pJB59 encoding the insulin precursor B$_{chain}$(1–27)-Asp Lys Ala Ala Lys-A$_{chain}$(1–21) N-terminally fused to the 85 residues which make up the α-factor signal/leader peptide in which Leu in position 82 and Asp in position 83 have been substituted by Met and Ala, respectively (SEQ ID NOS.95 and 96).

FIG. 4 shows the DNA sequence of pAK623 encoding GLP-1$_{7-36Ala}$ N-terminally fused to the synthetic signal/leader sequence "YAP3/S1$_{PAVA}$" (SEQ ID NOS.97 and 98).

FIGS. 5–6 shows the DNA sequence of pKV142 encoding B$_{chain}$(1–29)-Ala-Ala-Arg-A$_{chain}$(1–21) N-terminally fused to the 85 residues which make up the α-factor signal/leader peptide in which Leu in position 82 and Asp in position 83 have been substituted by Met and Ala, respectively (SEQ ID NOS.95 and 96).

FIGS. 7–8 shows the DNA sequence of pAK679 encoding $B_{chain}$(1–29)-Ala-Ala-Lys-$A_{chain}$(1–21) N-terminally fused to the synthetic signal/leader sequence "YAP3/LA19" (SEQ ID NOS.99 and 100).

FIG. 14 is the DNA and amino acid sequences in pAK729 encoding the YAP3 signal peptide (amino acid No. 1 through 21), LA19 leader peptide (amino acid No. 22 through 64), N-terminal extension Glu Glu Ala Glu Pro Lys (amino acid No. 65 through 70), MI3 insulin precursor $B_{chain}$(1–29)-Ala-Ala-Lys-$A_{chain}$(1–21) (amino acid No. 71 through 123) (SEQ ID NOS. 101 and 102).

FIG. 16 shows the DNA and amino acid sequences in pAK773 encoding the YAP3 signal peptide, LA19 leader peptide, N-terminal extension Glu Glu Gly Glu Pro Lys, MI3 insulin precursor $B_{chain}$(1–29)-Ala Ala Lys-$A_{chain}$ (1–21) (SEQ ID NOS. 103 and 104).

FIG. 17 is the DNA and amino acid sequences in pAK749 encoding the YAP3 signal petide-LA19 leader Glu Glu Ala Glu Pro Lys-MI5 insulin precursor complex (SEQ ID NOS.105 and 106).

FIG. 18 is the DNA and amino acid sequences in pAK866 encoding the YAP3 signal petide-LA19 leader Glu Glu Ala Glu Pro Lys-X14 insulin precursor complex (SEQ ID NOS.107 and 108).

FIG. 19 is the LA19 leader DNA sequence (SEQ ID NO.109).

FIG. 21 is the DNA sequence encoding the YAP3 signal peptide-LA19 leader Glu Glu Gly Glu Pro Lys-MI3 insulin precursor complex (Example 17 below) (SEQ ID NOS.110 and 111).

DETAILED DESCRIPTION OF THE INVENTION

Figure 1:
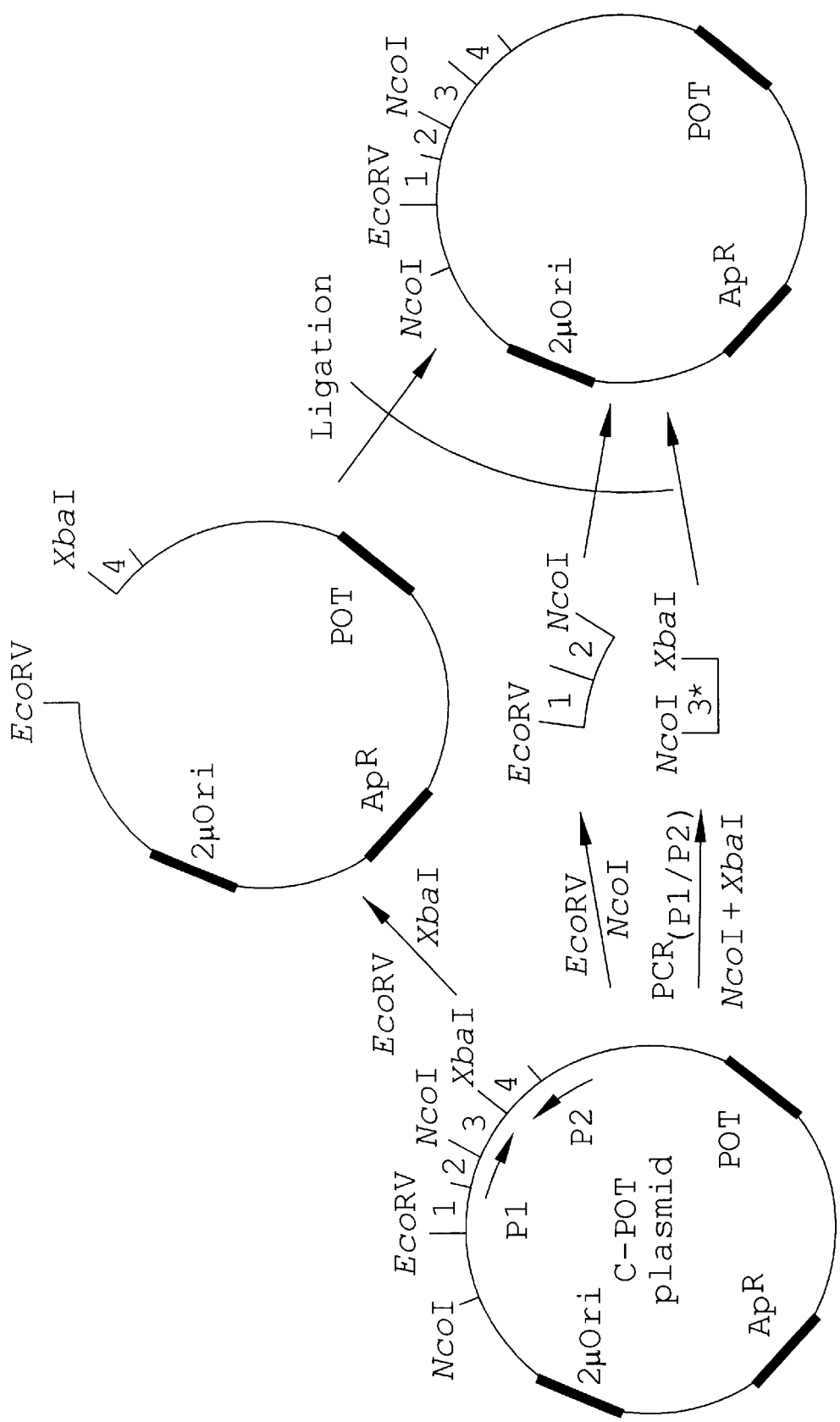
FIG. 1 shows a general scheme for the construction of plasmids containing genes expressing N-terminally extended polypeptides. 1 denotes the TPI gene promoter sequence from S. cerevisiae; 2 denotes the region encoding a signal/leader peptide (e.g. from the α-factor gene of S. cerevisiae); 3 denotes the region encoding a heterologous polypeptide; 3* denotes the region encoding a N-terminal extended heterologous polypeptide; 4 denotes the TPI gene terminator sequence of S. cerevisiae; P1 denotes a synthetic oligonucleotide PCR primer determining the structure of the N-terminal extension; P2 denotes a universal PCR primer for the amplification of region 3. POT denotes TPI gene from S. pombe; 2μ Ori denotes a sequence from S. cerevisiae 2μ plasmid including its origin of DNA replication in S. cerevisiae; Ap$^R$ is the sequence from pBR322 /pUC13 including the ampicilli resistance gene and an origin of DNA replication in E. coli.

In the peptide structure (A-B)$_n$, n is preferably 2–4 and more preferably 3. In preferred polypeptides according to the invention $X^3$ may be Glu, A may be Glu, B may be Ala, $X^5$ may be a peptide bond or Glu, or Glu Pro Lys Ala, or $X^6$ may be Pro or a peptide bond.

Examples of possible N-terminal extensions $X^3$-$X^4$-$X^5$-$X^6$-$X^7$ are:

Glu Glu Ala Glu Ala Glu (Pro/Ala) (Glu/Lys) (Ala/Glu/Lys/Thr) Arg Ala Pro Arg (SEQ ID NO:42),
Glu Glu Ala Glu Ala Glu Pro Lys Ala (Thr/Pro) Arg (SEQ ID NO:43),
Glu Glu Ala Glu Ala Glu Ala Glu Pro Arg (SEQ ID NO:44),
Glu Glu Ala Glu Ala Glu Ala Glu Pro Lys (SEQ ID NO:45),
Glu Glu Ala Glu Ala Glu Ala Glu Arg (SEQ ID NO:46),
Glu Glu Ala Glu Ala Glu Ala (Asp/Ala/Gly/Glu) Lys (SEQ ID NO:47),
Glu Glu Ala Glu Ala Glu Ala (Pro/Leu/Ile/Thr) Lys (SEQ ID NO:48),
Glu Glu Ala Glu Ala Glu Ala Arg (SEQ ID NO:49),
Glu Glu Ala Glu Ala Glu (Glu/Asp/Gly/Ala) Lys (SEQ ID NO:50),
Glu Glu Ala Glu Ala Pro Lys (SEQ ID NO:51),
Glu Glu Ala Pro Lys (SEQ ID NO:52),
Asp Asp Ala Asp Ala Asp Ala Asp Pro Arg (SEQ ID NO:53),
Glu Glu Glu Glu Pro Lys (SEQ ID NO:54),
Glu Glu Glu Pro Lys (SEQ ID NO:55),
Asp Asp Asp Asp Asp Lys (SEQ ID NO:56), and
Glu Glu Pro Lys (SEQ ID NO:57).

The N-terminally extended heterologous protein produced by the method of the invention may be any protein which may advantageously be produced in yeast. Examples of such proteins are aprotinin, tissue factor pathway inhibitor or other protease inhibitors, and insulin or insulin precursors, insulin analogues, insulin-like growth factors, such as IGF I and IGF II, human or bovine growth hormone, interleukin, tissue plasminogen activator, glucagon, glucagon-like peptide-1 (GLP 1), glucagon-like peptide-2 (GLP 2), GRPP, Factor VII, Factor VIII, Factor XIII, platelet-derived growth factor, enzymes, such as lipases, or a functional analogue of any one of these proteins. Preferred proteins are precursors of insulin and insulin like growth factors, and peptides of the proglucagon family, such as glucagon, GLP 1, GLP 2, and GRPP, including truncated forms, such as GLP-1(1–45), GLP-1(1–39), GLP-1(1–38), GLP-1(1–37), GLP-1(1–36), GLP-1(1–35), GLP-1(1–34), GLP-1(7–45), GLP-1(7–39), GLP-1(7–38), GLP-1(7–37), GLP-1(7–36), GLP-1(7–35), and GLP-1(7–34).

In the present context, the term "functional analogue" is meant to indicate a polypeptide with a similar biological function as the native protein. The polypeptide may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

The precursors of insulin, including proinsulin as well as precursors having a truncated and/or modified C-peptide or completely lacking a C-peptide, precursors of insulin analogues, and insulin related peptides, such as insulin like growth factors, may be of human origin or from other animals and recombinant or semisynthetic sources. The cDNA used for expression of the precursors of insulin, precursors of insulin analogues, or insulin related peptides in the method of the invention include codon optimised forms for expression in yeast.

By "a precursor of insulin" or "a precursor an insulin analogue" is meant a single-chain polypeptide which by one or more subsequent chemical and/or enzymatical processes can be converted to a two-chain insulin or insulin analogue molecule having the correct establishment of the three disulphide bridges as found in natural human insulin. Preferred insulin precursors are MI1, B(1–29)-A(1–21); MI3, B(1–29)-Ala-Ala-Lys-A(1–21) (as described in e.g. EP 163 529); X14, B(1–27-Asp-Lys)-Ala Ala Lys-A(1–21) (as described in e.g. PCT publication No. 95/00550); B(1–27-Asp-Lys)-A(1–21); B(1–27-Asp-Lys)-Ser Asp Asp Ala Lys-A(1–21); B(1–29)-Ala Ala Arg-A(1–21) (described in PCT Publication No. 95/07931); MI5, B(1–29)-Ser Asp Asp Ala Lys-A(1–21); and B(1–29)-Ser-Asp Asp Ala Arg-A(1–21), and more preferably MI1, B(1–29)-A(1–21), MI3, B(1–29)-Ala Ala Lys-A(1–21) and MI5, B(1–29)-Ser Asp Asp Ala Lys-A(1–21).

Examples of insulins or insulin analogues which can be produced in this way are human insulin, preferably des(B30) human insulin, porcine insulin; and insulin analogues wherein at least one Lys or Arg is present, preferably insulin analogues wherein $Phe^{B1}$ has been deleted, insulin analogues wherein the A-chain and/or the B-chain have an N-terminal extension and insulin analogues wherein the A-chain and/or the B-chain have a C-terminal extension. Other preferred insulin analogues are such wherein one or more of the amino acid residues, preferably one, two, or three of them, have been substituted by another codable amino acid residue. Thus in position A21 a parent insulin may instead of Asn have an amino acid residue selected from the group comprising Ala, Gln, Glu, Gly, His, Ile, Leu, Met, Ser, Thr, Trp, Tyr or Val, in particular an amino acid residue selected from the group comprising Gly, Ala, Ser, and Thr. The insulin analogues may also be modified by a combination of the changes outlined above. Likewise, in position B28 a parent insulin may instead of Pro have an amino acid residue selected from the group comprising Asp and Lys, preferably Asp, and in position B29 a parent insulin may instead of Lys have the amino acid Pro. The expression "a codable amino acid residue" as used herein designates an amino acid residue which can be coded for by the genetic code, i. e. a triplet ("codon") of nucleotides.

The DNA construct of the invention encoding the polypeptide of the invention may be prepared synthetically by established standard methods, e.g. the phosphoamidite method described by Beaucage et al. (1981) Tetrahedron Letters 22:1859–1869, or the method described by Matthes et al. (1984) EMBO Journal 3:801–805. According to the phosphoamidite method, oligonucleotides are synthesized, e.g. in an automatic DNA synthesizer, purified, duplexed and ligated to form the synthetic DNA construct. A currently preferred way of preparing the DNA construct is by polymerase chain reaction (PCR), e.g. as described in Sambrook et al. supra.

The DNA construct of the invention may also be of genomic or cDNA origin, for instance obtained by preparing a genomic or cDNA library and screening for DNA sequences coding for all or part of the polypeptide or the invention by hybridization using synthetic oligonucleotide probes in accordance with standard techniques. In this case, a genomic or cDNA sequence encoding a signal and leader peptide may be joined to a genomic or cDNA sequence encoding the heterologous protein, after which the DNA sequence may be modified at a site corresponding to the amino acid extension sequence of the polypeptide, by inserting synthetic oligonucleotides encoding the desired amino acid sequence for homologous recombination in accordance with well-known procedures or preferably generating the desired sequence by PCR using suitable oligonucleotides.

Finally, the DNA construct may be of mixed synthetic and genomic, mixed synthetic and cDNA or mixed genomic and cDNA origin prepared by annealing fragments of synthetic, genomic or cDNA origin (as appropriate), the fragments corresponding to various parts of the entire DNA construct, in accordance with standard techniques. Thus, it may be envisaged that the DNA sequence encoding the heterologous protein may be of genomic or cDNA origin, while the sequence encoding the signal and leader peptide as well as the sequence encoding the N-terminal extension may be prepared synthetically.

In a further aspect, the invention relates to a recombinant expression vector which is capable of replicating in yeast and which carries a DNA construct encoding the above-defined polypeptide. The recombinant expression vector may be any vector which is capable of replicating in yeast organisms. In the vector, the DNA sequence encoding the polypeptide of the invention should be operably connected to a suitable promoter sequence. The promoter may be any DNA sequence which shows transscriptional activity in yeast and may be derived from genes encoding proteins either homologous or heterologous to yeast. The promoter is preferably derived from a gene encoding a protein homologous to yeast. Examples of suitable promoters are the *Saccharomyces cerevisiae* MΑ1, TPI, ADH or PGK promoters.

The DNA sequence encoding the polypeptide of the invention may also be operably connected to a suitable terminator, for example the TPI terminator (Alber et al. (1982) J. Mol. Appl. Genet. 1:419–434).

The recombinant expression vector of the invention comprises a DNA sequence enabling the vector to replicate in yeast. Examples of such sequences are the yeast plasmid 2µ replication genes REP 1–3 and origin of replication. The vector may also comprise a selectable marker, such as the *Schizosaccharomyces pompe* TPI gene (Russell (1985) Gene 40:125–130).

The procedures used to ligate the DNA sequences coding for the polypeptide of the invention, the promoter and the terminator, respectively, and to insert them into suitable yeast vectors containing the information necessary for yeast replication, are well known to persons skilled in the art (see for example, Sambrook et al. supra). It will be understood that the vector may be constructed either by first preparing a DNA construct containing the entire DNA sequence coding for the polypeptide of the invention and subsequently inserting this fragment into a suitable expression vector, or by sequentially inserting DNA fragments containing genetic information for the individual elements (such as the signal, leader or heterologous protein) followed by ligation.

The yeast organism used in the process of the invention may be any suitable yeast organism which, on cultivation, produces large amounts of the heterologous protein or polypeptide in question. Examples of suitable yeast organisms may be strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., and *Geotrichum fermentans.* The transformation of the yeast cells may for instance be effected by protoplast formation followed by transformation in a manner known per se. The medium used to cultivate the cells may be any conventional medium suitable for growing yeast organisms. The secreted heterologous protein, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The transformation of the yeast cells may for instance be effected by protoplast formation followed by transformation in a manner known per se. The medium used to cultivate the cells may be any conventional medium suitable for growing yeast organisms. The secreted heterologous protein, a significant proportion of which will be present in the medium in correctly processed form, may be recovered from the medium by conventional precedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

After secretion to the culture medium, the protein may be subjected to various precedures to remove the extension sequence.

The extension is found to be stably attached to the heterologous protein during fermentation, protecting the N-terminal of the heterologous protein against the proteolytic activity of yeast proteases such as DPAP. The presence of an N-terminal extension on the heterologous protein may also serve as a protection of the N-terminal amino group of the heterologous protein during chemical processing of the protein, i.e. it may serve as a substitute for a BOC (t-butyl-oxycarbonyl) or similar protecting group. In such cases the amino acid extension sequence may be removed from the recovered heterologous protein by means of a proteolytic enzyme which is specific for a basic amino acid (i.e. K (Lys)) so that the terminal extension is cleaved off at the K. Examples of such proteolytic enzymes are trypsin or *Achromobacter lyticus* protease I.

The present invention is described in further detain in the following examples which are not in any way intended to limit the scope of the invention as claimed.

EXAMPLES

Plasmids and DNA

All expressions plasmids are of the C-POT type (FIG. 1), similar to those described in WO EP 171 142, which are characterized by containing the *Schizosaccharomyces pombe* triose phosphate isomerase gene (POT) for the purpose of plasmid selection and stabilization in *S. cerevisiae*. The plasmids furthermore contain the *S. cerevisiae* triose phosphate isomerase promoter (region 1, FIG. 1) and terminator (region 4, FIG. 1). These sequences are identical to the corresponding sequences in plasmid pKFN1003 (described in WO 90/100075) as are all sequences except the sequence of the EcoRI-XbaI fragment encoding the signal/leader/product (region 2 and 3, FIG. 1). In order to express different heterologous proteins, the EcoRI-XbaI fragment of pKFN1003 is simply replaced by an EcoRI-XbaI fragment encoding the signal/leader/product of interest. Such EcoRI-XbaI fragments may be synthesized using synthetic oligonucleotides and PCR according to standard techniques.

FIG. 1 shows the general scheme used for the construction of plasmids containing genes expressing N-terminally extended polypeptides, the scheme including the following steps.

A sample of the C-POT plasmid vector is digested with restriction nucleases EcoRV and XbaI and the largest DNA fragment is isolated using standard molecular techniques (Sambrook et al. supra). Another sample of C-POT plasmid (which may be the same or different from the plasmid above) is digested with restriction nucleases EcoRV and NcoI and the fragment comprising region 1 and 2 is isolated.

PCR is performed using the Gene Amp PCR reagent kit (Perkin Elmer) according to the manufacturer's instructions and the synthetic oligonucleotide primers P1 and P2 on a template (which may be the same or different from the plasmids above) encoding the heterological polypeptide of interest. P1 is designed to include a recognition site for restriction nuclease NcoI (5'-CCATGG-3') (SEQ ID NO:58) followed by the sequences encoding a KEX2 processing site, the N-terminal extension and 10–15 nucleotides identical to the sequence encoding the original N-terminal of the heterologous protein of interest. P2 (5'-AATTTATTTTACATAACACTAG-3')(SEQ ID NO:59) amplifies region 3 and the flanking recognition site for restriction nuclease XbaI (5'-TCTAGA-3')(SEQ ID NO:60) in PCRs with P1 using standard techniques described in Sambrook et al., supra.

The PCR product is digested with restriction nucleases NcoI and XbaI and the digested fragment is isolated. The fragments isolated are ligated together by T4 DNA ligase under standard conditions (Sambrook et al. supra). The ligation mixture is used to transform competent *E. coli* cells ap$^{r-}$ and selected for ampicillin resistance. Plasmids are isolated from the resulting *E. coli* clones using standard molecular techniques. DNA Sequencing is performed using enzymatic chain termination in order to determine the DNA sequences encoding the N-terminal extended polypeptide and to ensure that it is in frame with the DNA sequence encoding the signal/leader peptide of region 2.

The plasmid is used to transform the yeast strain MT663 and selected for growth on glucose, as follows:

Yeast transformation: *S. cerevisiae* strain MT663 (E2-7B XE11–36 a/α, Δtpi/Δtpi, pep 4-3/pep 4-3) (the yeast strain MT663 was deposited in the Deutsche Sammlung von Mikroorganismen und Zellkulturen in connection with filing WO 92/11378 and was given the deposit number DSM 6278) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 µg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) *Methods in Yeast Genetics,* Cold Spring Harbor Laboratory) containing 1.2 M sorbitol plus 2.5% agar) at 52° C. was added and the suspension poured on top of plates containing the same agar-solidified, sorbitol containing medium.

Example 1

Construction of pJB108 and pJB109

Plasmid pJB59 is a derivative of pKFN1003 in which the EcoRI-XbaI fragment encodes the insulin precursor B$_{chain}$ (1–27)-Asp Lys Ala Ala Lys (SEQ ID NO:61)-A$_{chain}$(1–21)

N-terminally fused to a signal/leader sequence corresponding to the 85 residues of the α-factor prepro signal peptide in which Leu in position 82 and Asp in position 83 have been substituted by Met and Ala, respectively (FIGS. 2–3): The EcoRI-XbaI fragment is synthesized in an applied biosystems DNA synthesizer.

Plasmid constructs designed to express N-terminally extended insulin precursor $B_{chain}$(1–27)-Asp Lys Ala Ala Lys-(SEQ ID NO:61)$A_{chain}$(1–21) were obtained by means of a P1-primer with the following DNA (SEQ ID NO:62) and corresponding amino acid (SEQ ID NO:63) sequence

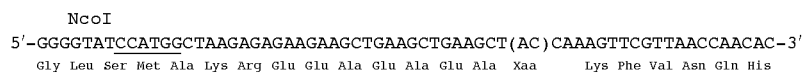

the P2-primer (SEQ ID NO:59) and the plasmid pJB59 according to the general scheme described above. PCR and cloning resulted in a construct wherein the DNA sequence encoding the insulin precursor $B_{chain}$(1–27)-Asp Lys Ala Ala Lys (SEQ ID NO:61)-$A_{chain}$(1–21) is preceded by a DNA sequence encoding the N-terminal extension Glu Glu Ala Glu Ala Glu Ala Xaa Lys (SEQ ID NO:64), where Xaa is either Pro (pJB108; Pro encoded by CCA) or Thr (pJB109; Thr encoded by ACA).

Example 2

Construction of pJB44, pJB107, and pJB126

Plasmid constructs designed to express additional N-terminally extended versions of the insulin precursor $B_{chain}$(1–27)-Asp Lys Ala Ala Lys (SEQ ID NO:61)-$A_{chain}$(1–21) were made by means of a P1-primer with the DNA (SEQ ID NO:65) and corresponding amino acid (SEQ ID NO:66) sequence

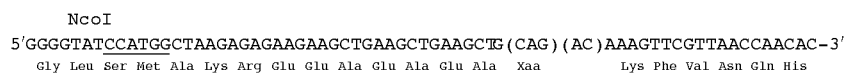

the P2-primer (SEQ ID NO:59) and the plasmid pJB59 as described in Example 1. Among the resulting plasmids pJB44, pJB107 and pJB126 where isolated. These plasmids encode the insulin precursor $B_{chain}$(1–27)-Asp Lys Ala Ala Lys-$A_{chain}$(1–21) preceded by the N-terminal extension Glu Glu Ala Glu Ala Glu Ala Xaa Lys (SEQ ID NO:64), where Xaa is either Glu (pJB44; Glu encoded by GAA), Asp (pJB126; Asp encoded by GAC) or Gly (pJB107; Gly encoded by GGC).

Example 3

Construction of pJB64 and pJB110

Plasmid constructs designed to express N-terminally extended insulin precursor $B_{chain}$(1–27)-Asp Lys Ala Ala Lys (SEQ ID NO:61)-$A_{chain}$(1–21) were obtained by means of a P1-primer with the following DNA (SEQ ID NO:67) and corresponding amino acid (SEQ ID NO:68) sequence

the P2-primer (SEQ ID NO:59) and the plasmid pJB59 as described in Example 1. Among the resulting plasmids pJB64 and pJB110 were isolated. These plasmids encode N-terminal extensions of $B_{chain}$(1–27)-Asp Lys Ala Ala Lys (SEQ ID NO:61)-$A_{chain}$(1–21) preceded by a DNA sequence encoding the N-terminal extension Glu Glu Ala Glu Ala Glu Xaa Lys (SEQ ID NO:69), where Xaa is either Glu (pJB110; Glu encoded by GAA) or Ala (pJB64; Ala encoded by GCA).

Example 4

Construction of pAK663

Plasmid pAK623 is a derivative of pKNF 1003 in which the EcoRI-XbaI fragment encodes GLP-1$_{7-36Ala}$ N-terminally fused to a synthetic signal leader sequence YAP3/S1$_{PAVA}$ (FIG. 4). The EcoRI-XbaI fragment was synthesized in an Applied Biosystems DNA synthesizer.

Plasmid constructs designed to express GLP-1$_{7-36ALA}$ with the N-terminal extension in form of Glu Glu Ala Glu Ala Glu Ala Glu Arg (SEQ ID NO:46) was obtained by means of a P1-primer with the following DNA (SEQ ID NO:70) and corresponding amino acid (SEQ ID NO:71) sequence

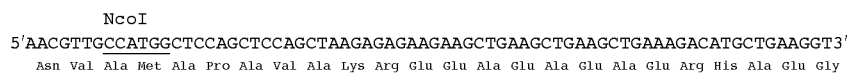

the P2-primer (SEQ ID NO:59) and the plasmid pAK623 according to the method described above resulting in plasmid pAK663.

Example 5
Expression of N-terminal Extended Products and the Removal of the Extensions Yeast strain MT663 transformed with the C-POT plasmids described above (pJB59, pJB108, pJB109, pJB44, pJB126, pJB107, pJB64 and pJB110) were grown on YPD (1% yeast extract, 2% peptone and 2% glucose) agar plates. Single colonies were used to start 5 ml liquid cultures in YPD broth pH=6.0, which were shaken for 72 hours at 30° C. Yields of products were determined directly on culture supernatants by the method described by Snel et al. (1987) Chromatographia 24:329–332.

The results with the yeast strains expressing N-terminally extended $B_{chain}$(1–27)-Asp Lys Ala Ala Lys (SEQ ID NO:61)-$A_{chain}$(1–21) compared to the non-extended form (pJB59) are shown below

| Plasmid | N-terminal extension | Yield |
|---|---|---|
| pJB59 | | 100% |
| pJB108 | Glu Glu Ala Glu Ala Glu Ala Pro Lys (SEQ ID NO:72) | 275% |
| pJB109 | Glu Glu Ala Glu Ala Glu Ala Thr Lys (SEQ ID NO:73) | 300% |
| pJB44 | Glu Glu Ala Glu Ala Glu Ala Glu Lys (SEQ ID NO:74) | 325%* |
| pJB126 | Glu Glu Ala Glu Ala Glu Ala Asp Lys (SEQ ID NO:75) | 300% |
| pJB107 | Glu Glu Ala Glu Ala Glu Ala Gly Lys (SEQ ID NO:76) | 275% |
| pJB64 | Glu Glu Ala Glu Ala Glu Ala Lys (SEQ ID NO:77) | 250%* |
| pJB110 | Glu Glu Ala Glu Ala Glu Glu Lys (SEQ ID NO:78) | 225%* |

Yields marked by (*) asterisk denotes that the product in these cases is a mixture of N-terminated extended $B_{chain}$ (1–27)-Asp Lys Ala Ala Lys(SEQ ID NO:61)-$A_{chain}$(1–21) and non-extended $B_{chain}$(1–27)-Asp Lys Ala Ala Lys (SEQ ID NO:61)-$A_{chain}$(1–21), the latter being a result of the in vivo cleavage of the extension described below and illustrated in FIGS. 5–8.

In case of pAK663 expressing GLP-$1_{7-36Ala}$ N-terminally extended by Glu Glu Ala Glu Ala Glu Ala Arg (SEQ ID NO:49) the yield was found to be 20 fold higher than pAK623 expressing non-extended GLP-$1_{7-36Ala}$.

Example 6
Removal of N-terminal Extensions in vivo

Culture supernatants obtained from cultures of yeast strains transformed with plasmid pJB59, pJB64, pJB44 and pJB108 (see above) were evaluated by HPLC chromatography (FIGS. 9–11) and parallel samples were run on a 10% Tricine-SDS-PAGE gel. From the HPLC chromatograms it appears that the culture supernatants from yeasts with plasmid pJB44 (chromatogram 3) and pJB64 (chromatogram 2) contain both the N-terminally extended as well as non-extended $B_{chain}$(1–27)Asp Lys Ala Ala Lys(SEQ ID NO:61)-A(1–21), whereas culture supernatants from yeast with pJB108 chromatogram 4) only contain the N-terminally extended form. In case of pJB64 about 50% of the precursor is found in non-extended form, whereas this form only represent a minor part of pJB44.

These results illustrate the ability of yeast to cleave off N-terminal extensions selectively in vivo when the extension is either Glu Glu Ala Glu Ala Glu Ala Lys (SEQ ID NO:77) (pJB64) or Glu Glu Ala Glu Ala Glu Ala Glu Lys (SEQ ID NO:74) (pJB44) and the inability of yeast to cleave off an N-terminal extension in the form of Glu Glu Ala Glu Ala Glu Ala Pro Lys (SEQ ID NO:72) (pJB108). The proteolytic activity responsible for cleaving off the extensions may be associated with enzymes in the secretory pathway such as membrane-bound YAP3 in the trans-Golgi system of the yeast cells.

Example 7
Removal of N-terminal Extensions in vitro

The culture supernatants described above were used as substrates for proteolytic cleavage with either partially purified YAP3 enzyme isolated from yeast strain ME783 overexpressing YAP3 or *Achromobacter lyticus* protease I.

YAP3 assay was performed as follows: 4 μl of YAP3 enzyme, 800 μl of cell free growth media. Samples were incubated for 15 h at 37° C. in 0.1 M Na citrate buffer, pH 4.0.

*Achromobacter lyticus* protease I assay performed as follows:
10 μg *A. lyticus* protease I
1 ml of cell free growth media
Samples were incubated for 1 h at 37° C. in 0.1 M Tris buffer, pH 8.75

Figure 9:
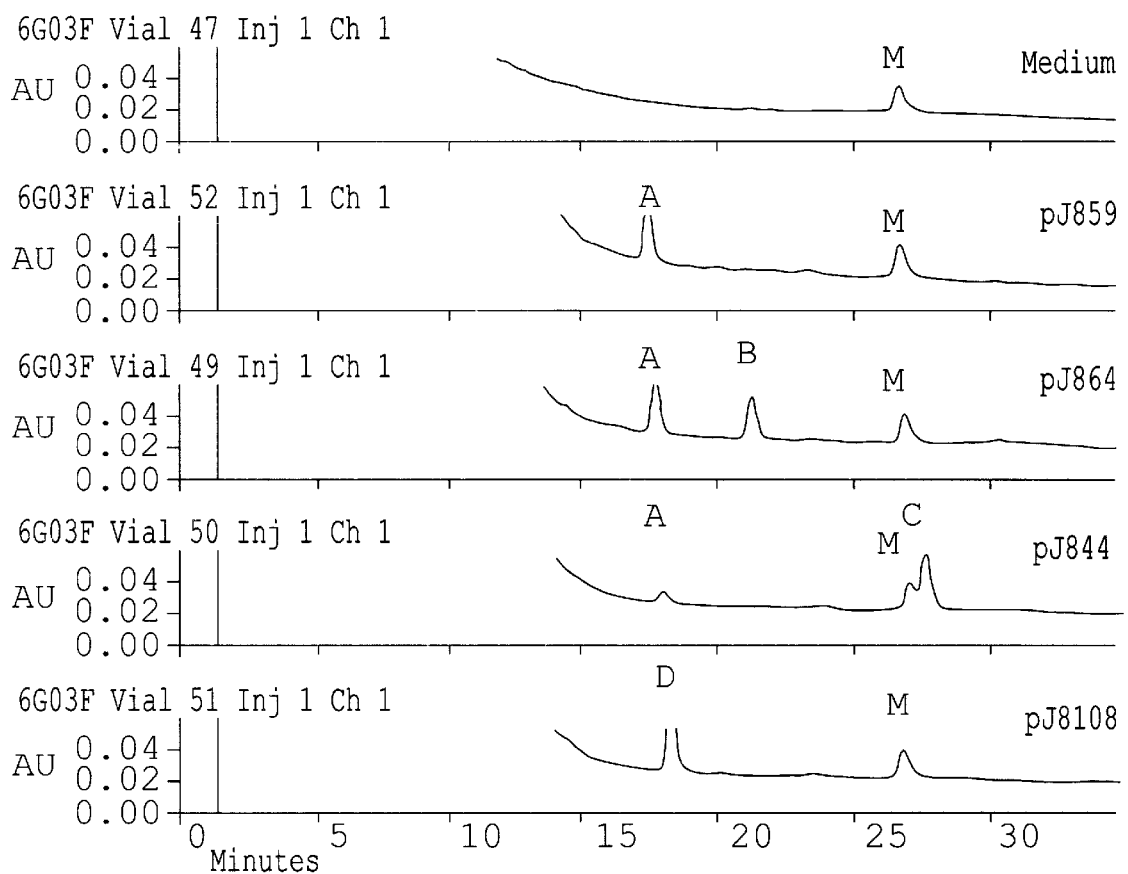
FIGS. 9–11 shows HPLC chromatograms of culture supernatants containing the insulin precursor $B_{chain}$(1–27) Asp Lys Ala Ala Lys-$A_{chain}$(1–21) with or without N-terminal extensions; and with or without in vivo or in vitro processing of the N-terminal extensions.
Figure 10:
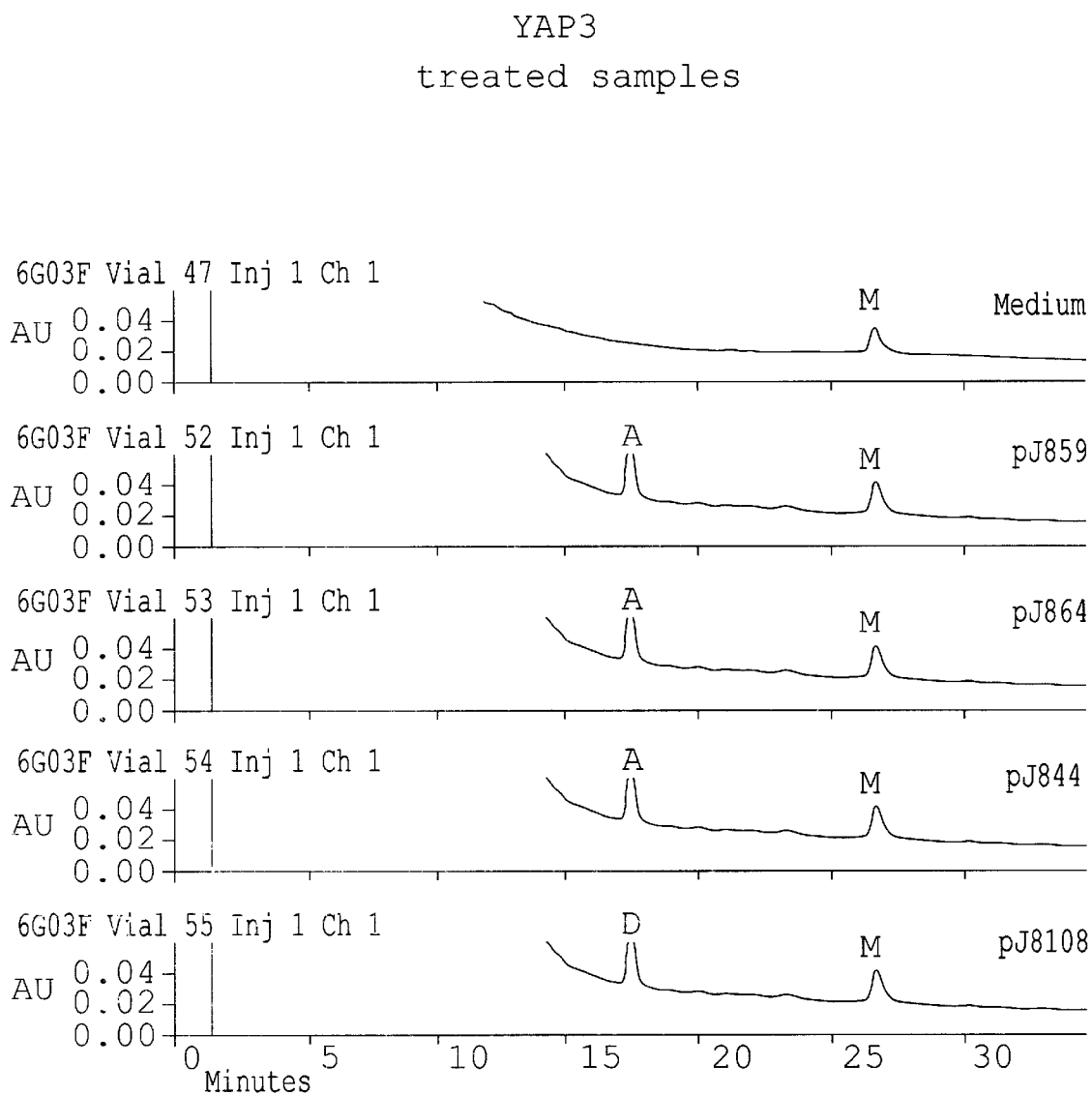
Figure 11:
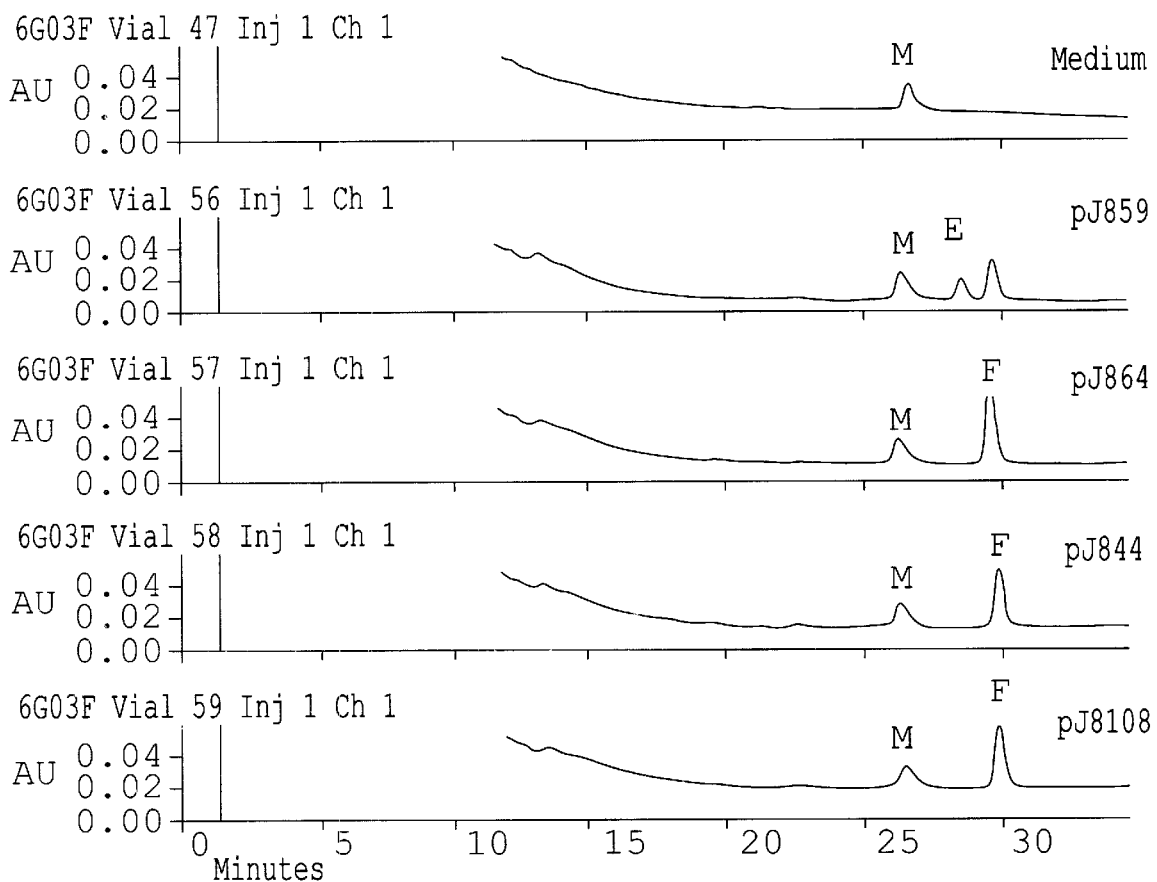

FIGS. 9–11 show the results evaluated by HPLC chromatography obtained from the YAP3 and *A. lyticus* protease I digestions, respectively. Parallel samples were run on 10% Tricine-SDS-PAGE.

From the chromatograms it appears that the YAP3 enzyme is able to cleave off N-terminal extensions selectively when these are in form of Glu Glu Ala Glu Ala Glu Ala Lys (SEQ ID NO:77) (pJB64) or Glu Glu Ala Glu Ala Glu Ala Glu Lys (SEQ ID NO:74) (pJB44) but not Glu Glu Ala Glu Ala Glu Ala Pro Lys (SEQ ID NO:72) (pJB108). This results clearly indicates that YAP3 or YAP3-like enzyme(s) are responsible for the partial cleavage of N-terminal extensions seen in vivo.

From the chromatograms it appears that digestions with *A. lyticus* protease I in all cases result in the same product, namely $B_{chain}$(1–27)-Asp-Lys-(connected by disulfide bonds)-$A_{chain}$(1–21) which is the end result of proteolytic cleavage after all Lys-residues found in the $B_{chain}$(1–27)Asp Lys Ala Ala Lys (SEQ ID NO:61)-$A_{chain}$(1–21) insulin precursor including those found between the B and A chain in the precursor.

In the case of the digestion of the culture supernatant from yeast transformed with pJB59 (expressing the non-extended $B_{chain}$(1–27)Asp Lys Ala Ala Lys(SEQ ID NO:61)-$A_{chain}$ (1–21)) a product is seen which does not appear in the other digestions. This product, Arg-$B_{chain}$(1–27)-Asp-Lys-(connected by disulfide bonds)-$A_{chain}$(1–21), results from *A. lyticus* protease I cleavage of secreted leader-precursor in the growth media. *A. lyticus* protease I cleaves between the Lys and Arg residues in the dibasic KEX2 site of the product which has escaped KEX2 cleavage in the secretory pathway of the yeast cells.

Example 8
Removal of N-terminal Extensions by Over-expressing YAP3

The YAP3 gene was inserted into the C-POT plasmid pJB64 encoding Glu Glu Ala Glu Ala Glu Ala Lys(SEQ ID NO:77)-$B_{chain}$(1–27)-Pro Lys Ala Ala Lys(SEQ ID NO:78)-$A_{chain}$(1–21) (see Example 3) in the following way:

The 2.5 kb SalI/SacI fragment containing the YAP3 gene was isolated from plasmid pME768 and inserted into the SalI and SacI site of plasmid pIC19R (March et al. 1984 Gene:32:481–485). From the resulting plasmid designated pME834 a 2.5 kb SalI/XhoI fragment containing the YAP3 gene was isolated and inserted into the unique SalI site placed between the POT and the ApR sequences of pJB64. One resulting plasmid was designated pJB176.

Figure 12:
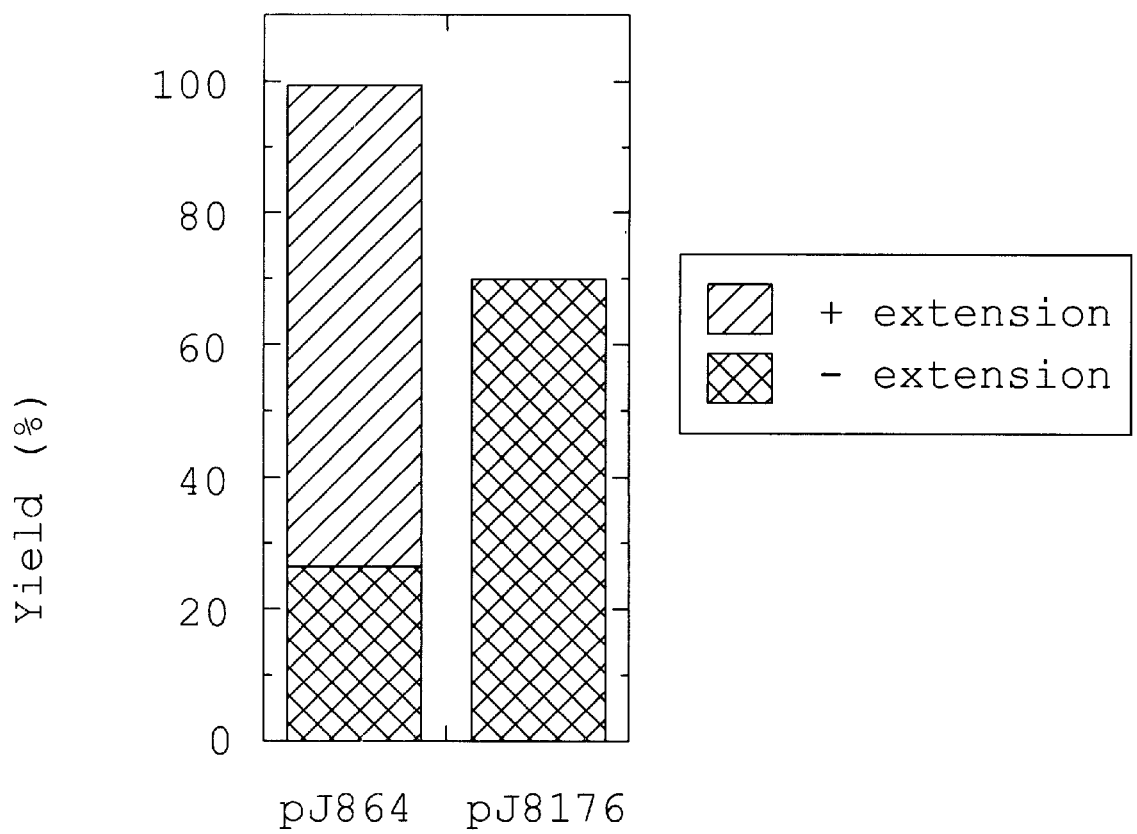
FIG. 12 shows the effect of the presence of YAP3 coexpression on the yield derived from the HPLC data in pJB176 compared to pJB64.
Figure 13:
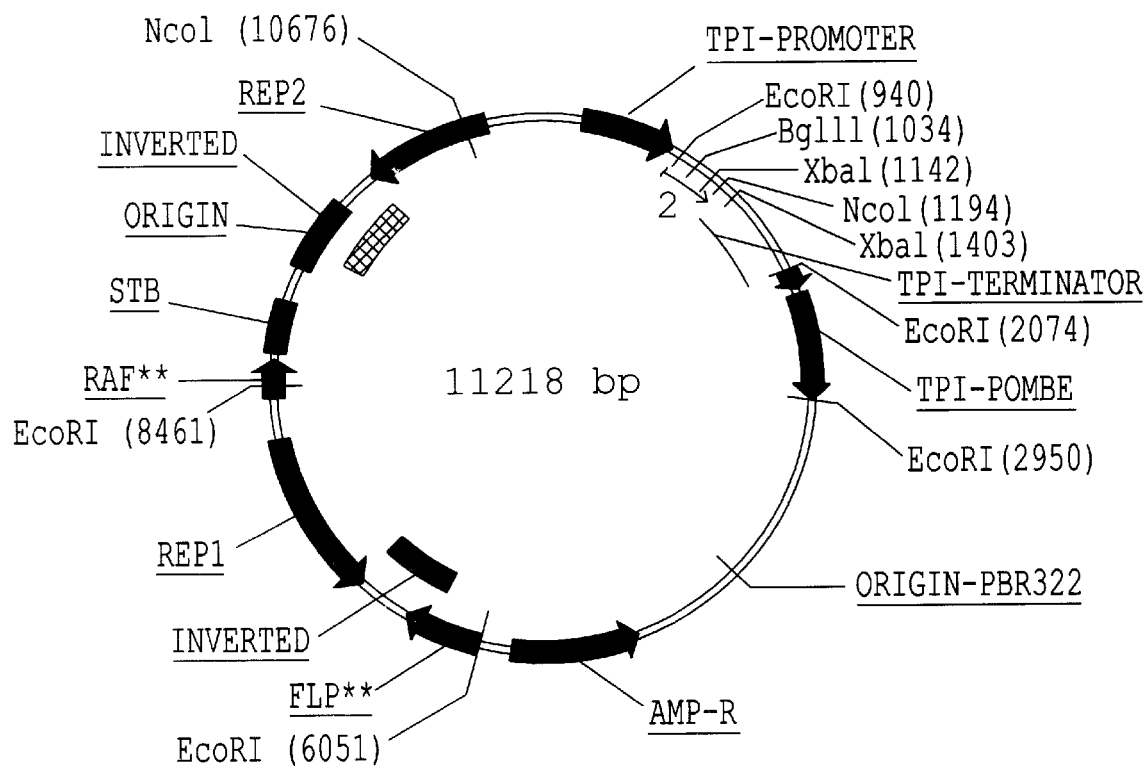
FIG. 13 shows the expression plasmid pAK729 containing genes expressing the N-terminally extended polypeptides of the invention. TPI-PROMOTER: Denotes the TPI gene promoter sequence from S. cerevisiae; 2: Denotes the region encoding a signal/leader peptide; TPI-TERMINATOR: Denotes TPI gene terminator sequence of S. cerevisiae; TPI-POMBE: Denotes TPI gene from S. pombe; Origin: Denotes a sequence from S. cerevisiae 2μ plasmid including its origin of DNA replication in S. cerevisiae; AMP-R: Sequence from pBR322 /pUC13 including the ampicillin resistance gene and an origin of DNA replication in E. coli.

Yeast strain MT663 was transformed with pJB176 and analyzed as described below. As can be seen from the HPLC data on yield shown in FIG. 12 the presence of the YAP3 gene in pJB176 clearly effects a higher percent of non-extended $B_{chain}$(1–27)-Pro Lys Ala Ala Arg(SEQ ID NO:79)-$A_{chain}$(1–21) in the culture-supernatant of the corresponding yeast transformants compared to the yeast transformant of pJB64.

This result illustrates the ability to make yeast strains with an enhanced capacity to cleave off N-terminal extensions selectively in vivo by manipulating the level of proteolysis caused by YAP3.

Example 9
Construction of pKV143

Plasmid pKV142 is a derivative of pKFN1003 in which the EcoRI-XbaI fragment encodes the insulin precursor $B_{chain}$(1–29)-Ala Ala Arg-$A_{chain}$(1–21) N-terminally fused to a signal/leader sequence corresponding to the 85 residues of the α-factor prepro signal peptide in which Leu in position 82 and Asp in position 83 have been substituted by Met and Ala, respectively (FIG. 5–6).

Plasmid constructs designed to express B. (1–29)-Ala Ala Arg-$A_{chain}$(1–21) with a N-terminal extension in form Asp Asp Ala Asp Ala Asp Ala Asp Pro Arg (SEQ ID NO:53) was obtained by means of a P1-primer with the following DNA (SEQ ID NO:80) and corresponding amino acid (SEQ ID NO:81) sequence

```
        NcoI
5'-GGGGTATCCATGGCTAAGAGAGACGACGCTGACGCTGACGCTGACCCAAGATTCGTTAACCAACACTTGTGCGG-3'
   Gly Leu Ser Met Ala Lys Arg Asp Asp Ala Asp Ala Asp Ala Asp Pro Arg Phe Val Asn Gln His Leu Cys
``` the P2-primer (SEQ ID NO:59) and the plasmid pKV142.

Example 10
Construction of pKV102

Plasmid constructs designed to express $B_{chain}$(1–29)-Ala Ala Arg-$A_{chain}$(1–21) with a N-terminal extension in form Glu Glu Ala Glu Ala Glu Ala Glu Pro Lys Ala Thr Arg (SEQ ID NO:82) was obtained by means of a P1-primer with the following DNA (SEQ ID NO:83) and corresponding amino acid (SEQ ID NO:84) sequence

Example 11
Expression of N-terminal Extended $B_{chain}$(1–29)-Ala-Ala-Arg-$A_{chain}$(1–21)

Yeast strain MT663 transformed with the C-POT plasmids pKV142 pKV143 and pKV102 and analyzed as described in Example 5.

The results with the yeast strains expressing N-terminally extended $B_{chain}$(1–29)-Ala Ala Arg-$A_{chain}$(1–21) compared to the non-extended form (pKV142) are shown below

| Plasmid | N-terminal extension | Yield |
|---|---|---|
| pKV142 | | 100% |
| pKV143: | Asp Asp Ala Asp Ala Asp Ala Asp Pro Arg (SEQ ID NO:53) | 263% |
| pKV102: | Glu Glu Ala Glu Ala Glu Ala Glu Pro Lys Ala Thr Arg (SEQ ID NO:82) | 400% |

Example 12
Construction and Expression of pIM69 and pIM70

Plasmid pAK679 is a derivative of pKFN1003 in which the EcoRI-XbaI fragment encodes the insulin precursor $B_{chain}$(1–29)-Ala Ala Lys-$A_{chain}$(1–21) N-terminally fused to a synthetic signal/leader sequence YAP3/LA19 (FIG. 7–8).

Plasmid constructs designed to express N-terminally extended insulin precursor $B_{chain}$(1–29)-Ala Ala Lys-$A_{chain}$(1–21) were obtained by a procedure involving two successive PCR reaction. The first PCR reaction was performed by means of the primer with the following DNA (SEQ ID NO:85) and corresponding amino acid (SEQ ID NO:86) sequence

```
5'-GAAGAAGAAGAAGAAGAACCAAAGTTCGTTAACCAACAC-3'
   Glu Glu Glu Glu Glu Glu Pro Lys Phe Val Asn Gln His
``` the P2-primer (SEQ ID NO:59) and the plasmid pAK679.

The second PCR reaction was performed by means of the P1-primer (SEQ ID NO:87) and corresponding amino acid sequence (SEQ ID NO:88)

```
        NcoI
5'-GGGGTATCCATGGCTAAGAGAGAAGAAGCTGAAGCTGAAGCTGAAGCCAAAGGCTACAAGATTCGTTAACCAACACTTGTGCGG-3'
   Gly Leu Ser Met Ala Lys Arg Glu Glu Ala Glu Glu Ala Glu Ala Glu Ala Glu Pro Lys Ala Thr Arg Phe Val Asn Gln His Leu Cys
``` the P2-primer (SEQ ID NO:59) and the plasmid pKV142.

```
                          NcoI
5'-GTTGTTAACTTGATCTCCATGGCTAAGAGAGAAGAA-3'
   Val Val Asn Leu Ile Ser Met Ala Lys Arg Glu Glu
``` the P2-primer (SEQ ID NO:59) using the PCR product of the first PCR reaction as the DNA-template for the second PCR reaction.

The PCR product of the second PCR reaction was cut with NcoI and XbaI and ligated into pAK679 according to the general scheme described above. Among the resulting plasmids two where identified to encode N-terminal extensions of $B_{chain}$(1–29)-Ala-Ala-Lys-$A_{chain}$(1–21) in form of Glu Glu Glu Pro Lys (SEQ ID NO:55) (pIM70) and Glu Glu Glu Glu Pro Lys (SEQ ID NO:54), respectively.

Yeast strain MT663 was transformed with the C-POT plasmids pAK579, pIM69 and pIM70 and analyzed as described in Example 5.

Whereas the yield of non-extended $B_{chain}$(1–29)-Ala Ala Lys-$A_{chain}$(1–21) from yeast with pAK579 was found to be practicably nothing, yeast with pIM69 and pIM70 was found to produce large quantity of Glu Glu Glu Glu Pro Lys (SEQ ID NO:54)-$B_{chain}$(1–29)-Ala Ala Lys $A_{chain}$(1–21) and Glu Glu Glu Pro Lys(SEQ ID NO:55)-$B_{chain}$(1–29)-Ala Ala Lys-$A_{chain}$(1–21) respectively.

Example 13
Construction of the Yeast Strain yAK729 Expressing the Glu Glu Ala Glu Pro Lys (SEQ ID NO:1)-MI3 Insulin Precursor A synthetic gene coding for the N-terminal extension of N-terminally extended insulin precursor Glu Glu Ala Glu Pro Lys (SEQ ID NO:1)-MI3 was constructed using PCR.

The following 2 oligonucleotides were synthesized:
672 5'-TCTCCATGGCTAAGAGAGAAGAAGCTGAA-CCAAAGTTCGTT-3'(SEQ ID NO:89)
2785 5'-AATTTATTTTACATAACACTAG-3'(SEQ ID NO:90)

Oligonucleotides were synthesized using an automatic DNA synthesizer (applied Biosystems model 380A) using phosphoamidite chemistry and commercially available reagents. The following PCR was performed using the Pwo DNA Polymerase (Boehringer)and the PCR mix was overlayed with 100 μl mineral oil (Sigma). PCR: 5 μl oligonucleotide #672 (50 pmol), 5 μl oligonucleotide #2785 (50 pmol), 10 μl 10×PCR buffer, 8 μl dNTP mix, 0.5 μl Pwo enzyme 0.5 μl pAK680 plasmid as template (0.2 ug DNA), 71 μl dest. water. A total of 12 cycles were performed, one cycle was 94 C. for 45 se.; 40 C. for 1 min; 72 C. for 1.5 min. The PCR mixture was then loaded onto a 2.5% agarose gel and electroforese was performed using standard techniques. The resulting DNA fragment was cut out of the agarose gel and isolated by the Gene Clean Kit (Bio 101 inc.). The purified PCR DNA fragment was dissolved in 14 μl of water and restriction endonucleases buffer and cut with the restriction endonucleases NcoI and XbaI. The NcoI-XbaI DNA fragment on 209 nucleotide base pairs was subjected to agarose electroforesis and purified. The plasmid pAK721 was cut with the restriction endonucleases BglII and XbaI and the vector fragment of 10849 nucleotide base pairs isolated. The plasmid pAK721 was cut with the restriction endonucleases BglII and NcoI and the DNA fragment of 160 nucleotide base pairs isolated. The three DNA fragments was ligated together using T4 DNA ligase. The ligation mix was then transformed into a competent *E. coli* strain (R–, M+) followed by selection with ampicillin resistance.

Plasmid from the resulting *E. coli* was isolated and checked for insert with appropriate restriction endonucleases (Nco I and XbaI). The selected plasmid was shown by DNA sequence analysis (Sequenase) to encode the correct DNA sequence for the Glu Glu Ala Glu Pro Lys-MI3 insulin precursor DNA and to be inserted after the DNA encoding the synthetic LA19 leader DNA. The plasmid was named pAK729.

The DNA sequence encoding the YAP3 signal peptide-LA19 leader Glu Glu Ala Glu Pro Lys-MI3 insulin precursor complex is shown in FIG. 14.

The plasmid pAK721 was transformed into *S. cerevisiae* strain MT663 as described in PCT/DK95/00250 and the resulting strain was named yAK721.

The yeast expression plasmid pAK729 is of the C-POT type and is similar to those described in WO EP 171 142. pAK729 also contain the *S. cerevisiae* triose phosphate isomerase promoter and terminator. The promoter and terminator are similar to those described in the plasmid pKFN1003 (described in WO 90/100075) as are all sequences in plasmid except the sequence between the EcoRIXbaI fragment encoding the YAP3 signal peptide-LA19 leader peptide-Glu Glu Ala Glu Pro Lys-MI3 insulin precursor.

Example 14
Construction of the Yeast Strain yAK733 Expressing the Glu Glu Ala Glu Pro Lys-MI1 Insulin Precursor A synthetic gene coding for the N-terminal extension of N-terminally extended insulin precursor Glu Glu Ala Glu Pro Lys (SEQ ID NO:1)-MI1 was constructed by combining DNA fragments encoding leader and extension and insulin precursor.

Figure 15:
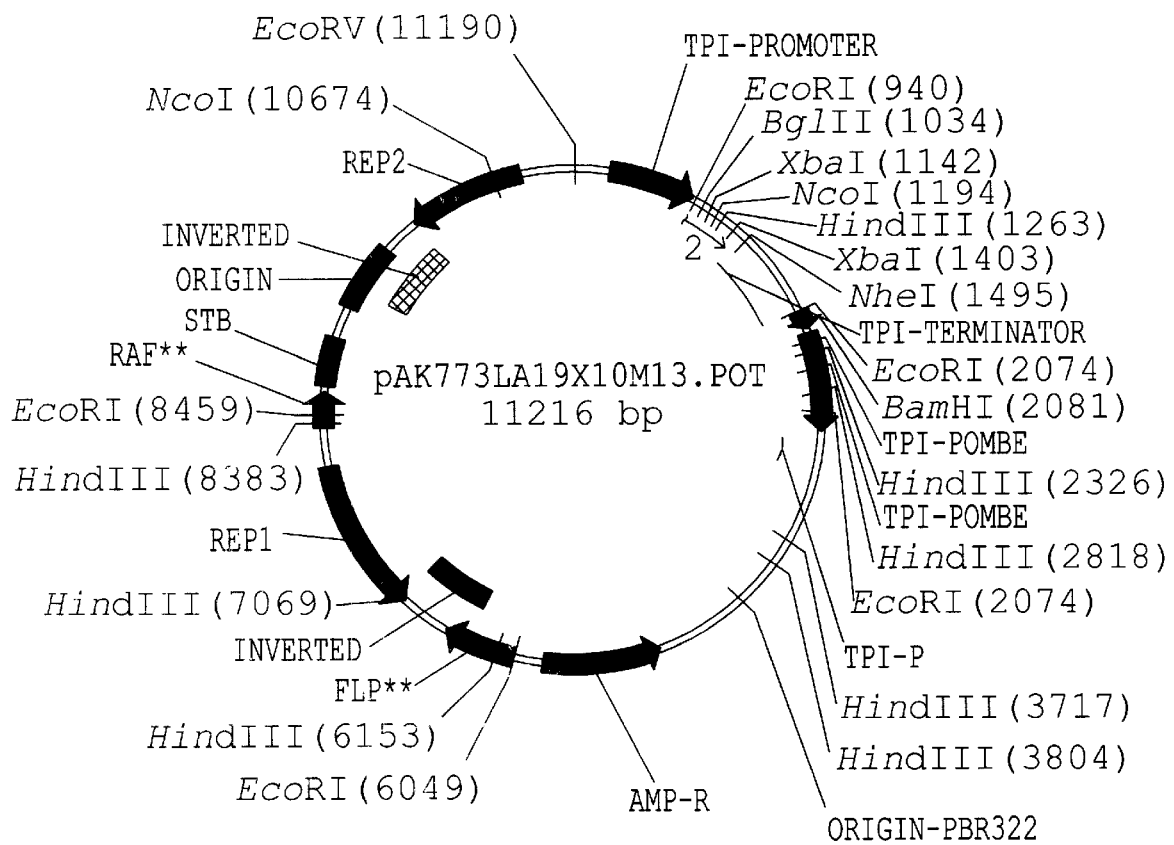
FIG. 15 shows the expression plasmid pAK773 containing genes expressing the N-terminally extended polypeptides of the invention. The symbols used are as described in the legend of FIG. 13, with 2: Denotes the region encoding a signal/leader peptide (e.g. from the YAP3 signal peptide and LA19 leader peptide in conjunction with the Glu Glu Gly Glu Pro Lys (SEQ ID NO:2) N-terminally extended MI3 insulin precursor.

The plasmid pAK721 was cut with the restriction endonucleases BglII and XbaI and the vector fragment of 10849 nucleotides isolated. The plasmid pAK730 was cut with the restriction endonucleases HindIII and XbaI and the DNA fragment of 131 nucleotides isolated. The plasmid pAK729 was cut with the restriction endonucleases BglII and HindIII and the DNA fragment of 229 nucleotides isolated. The three DNA fragments was ligated together using T4 DNA ligase, and the ligation mix was transformed into a competent *E. coli* strain (R–, M+) followed by selection with ampicillin resistance, as described above. Plasmid from the resulting *E. coli* was isolated uand checked for insert with appropriate restrictions endonucleases. The selected plasmid was shown by DNA sequence analysis to encode the correct DNA sequence for the Glu Glu Ala Glu Pro Lys-MI1 insulin precursor DNA and to be inserted after the DNA encoding the synthetic LA19 leader and extension DNA. The plasmid was named pAK733 (FIG. 15).

The DNA sequence encoding the YAP3 signal petide-LA19 leader Glu Glu Ala Glu Pro Lys-MI1 insulin precursor complex is shown in FIG. 16.

The plasmid pAK733 was transformed into *S. cerevisiae* strain MT663 as described in PCT/DK95/00250 and the resulting strain was named yAK733. The yeast expression plasmid pAK733 is of the C-POT type and is similar to those described in WO EP 171 142.

Example 15
Construction of the Yeast Strain yAK749 Expressing the Glu Glu Ala Glu Pro Lys-MI5 Insulin Precursor A synthetic gene coding for the N-terminal extension of N-terminally extended insulin precursor Glu Glu Ala Glu Pro Lys (SEQ ID NO:1)-MI5 was constructed by combining DNA fragment encoding leader and extension and insulin precursor.

The plasmid pAK743 was cut with the restriction endonucleases BglII and NheI and the vector fragment of 10757 nucleotides isolated. The plasmid pAK405 was cut with the restriction endonucleases HindIII and NheI and the DNA fragment of 238 nucleotides isolated. The plasmid pAK729 was cut with the restriction endonucleases BglII and HindIII and the DNA fragment of 229 nucleotides isolated. The three DNA fragments was ligated together using T4 DNA ligase as described above, and transformed into a competent *E. coli* strain (R−, M+) followed by selection with ampicillin resistance. Plasmid from the resulting *E. coli* was isolated, and checked for insert with appropriate restrictions endonucleases. The selected plasmid was shown by DNA sequence analysis to encode the correct DNA sequence for the Glu Glu Ala Glu Pro Lys-MI5 insulin precursor DNA and to be inserted after the DNA encoding the synthetic LA19 leader and extension DNA. The plasmid was named pAK749.

The DNA sequence encoding the YAP3 signal petide-LA19 leader Glu Glu Ala Glu Pro Lys-MI5 insulin precursor complex are shown in FIG. 17.

The plasmid pAK749 was transformed into *S. cerevisiae* strain MT663 as described in PCT/DK95/00250 and the resulting strain named yAK749. The yeast expression plasmid pAK749 is of the C-POT type and is similar to those described in WO EP 171 142.

Example 16
Construction of the Yeast Strain yAK866 Expressing the Glu Glu Ala Glu Pro Lys-X14 Insulin Precursor A synthetic gene coding for the N-terminal extension of N-terminally extended insulin precursor Glu Glu Ala Glu Pro Lys-X14 was constructed by combining DNA fragment encoding leader and extension and X14 insulin precursor.

The plasmid pAK743 was cut with the restriction endonucleases BglII and NheI and the vector fragment of 10757 nucleotides isolated. The plasmid pAK602 was cut with the restriction endonucleases HindIII and NheI and the DNA fragment of 232 nucleotides isolated. The plasmid pAK729 was cut with the restriction endonucleases BglII and HindIII and the DNA fragment of 229 nucleotides isolated. The three DNA fragments was ligated, and transformed into a competent *E. coli* strain (R−, M+) followed by selection with ampicillin resistance. Plasmid from the resulting *E. coli* was isolated and checked for insert with appropriate restrictions endonucleases. The selected plasmid was shown by DNA sequence analysis to encode the correct DNA sequence for the Glu Glu Ala Glu Pro Lys-X14 insulin precursor DNA and to be inserted after the DNA encoding the synthetic LA19 leader and extension DNA. The plasmid was named pAK866.

The DNA sequence encoding the YAP3 signal petide-LA19 leader Glu Glu Ala Glu Pro Lys-X14 insulin precursor complex is shown in FIG. 18. FIG. 19 is the LA19 leader DNA sequence. The plasmid pAK866 was transformed into *S. cerevisiae* strain MT663 as described in PCT/DK95/00250 and the resulting strain was named yAK866. The yeast expression plasmid pAK866 is of the C-POT type and is similar to those described in WO EP 171 142. The promoter and terminator are similar to those described in the plasmid pKFN1003 (described in WO 90/100075) as are all sequences in plasmid except the sequence between the EcoRI-XbaI fragment encoding the YAP3 signal peptide-LA19 leader-Glu Glu Ala Glu Pro Lys-X14 insulin precursor.

Example 17
Construction of the Yeast Strain yAK773 Expressing the Glu Glu Gly Glu Pro Lys-MI3 Insulin Precursor A synthetic gene coding for the N-terminal extension of N-terminally extended insulin precursor Glu Glu Gly Glu Pro Lys-MI3 was constructed using PCR. The following 2 oligonucleotides were synthesized:
724 5'-GATfCTCCATGGCTAAGAGAGAAGAAXYT-GAACCAAAGTTCGTTAACC-3' (SEQ ID NO:91), wherein X is A or G and Y is T, A, or G, and
2371 5'-TTAATCTTAGTTTCTAGAGCCTGCGGG-3' (SEQ ID NO:92).

Oligonucleotides were synthesized using an automatic DNA synthesizer. The following PCR was performed using the Expand High Fidelity Enzyme mix (Boehringer Mannheim GmbH) and the PCR mix was overlayed with 100 ul mineral oil (Sigma). PCR: 5 µl oligonucleotide #724 (total 100 pmol), 5 µl oligonucleotide #2371 (total 100 pmol) 10 µl 10×PCR buffer, 8 µl dNTP mix, µl Expand High Fidelity Enzyme mix, 0.5 µl pAK729 plasmid as template (0.2 µg DNA), 70.75 µl distilled water.

A total of 18 cycles were performed, one cycle was 94° C. for 45 sec.; 37° C. for 1 min; 72° C. for 1.5 min. The PCR mixture was then loaded onto a 2.5% agarose gel and electroforesis was performed. The resulting DNA fragment was cut out of the agarose gel and isolated.

The purified PCR DNA fragment was dissolved in 14 µl of water and restriction endonucleases buffer and cut with the restriction endonucleases NcoI and XbaI. The NcoI-XbaI DNA fragment on 209 nucleotide base pairs was subjected to agarose electroforesis and purified.

Figure 20:
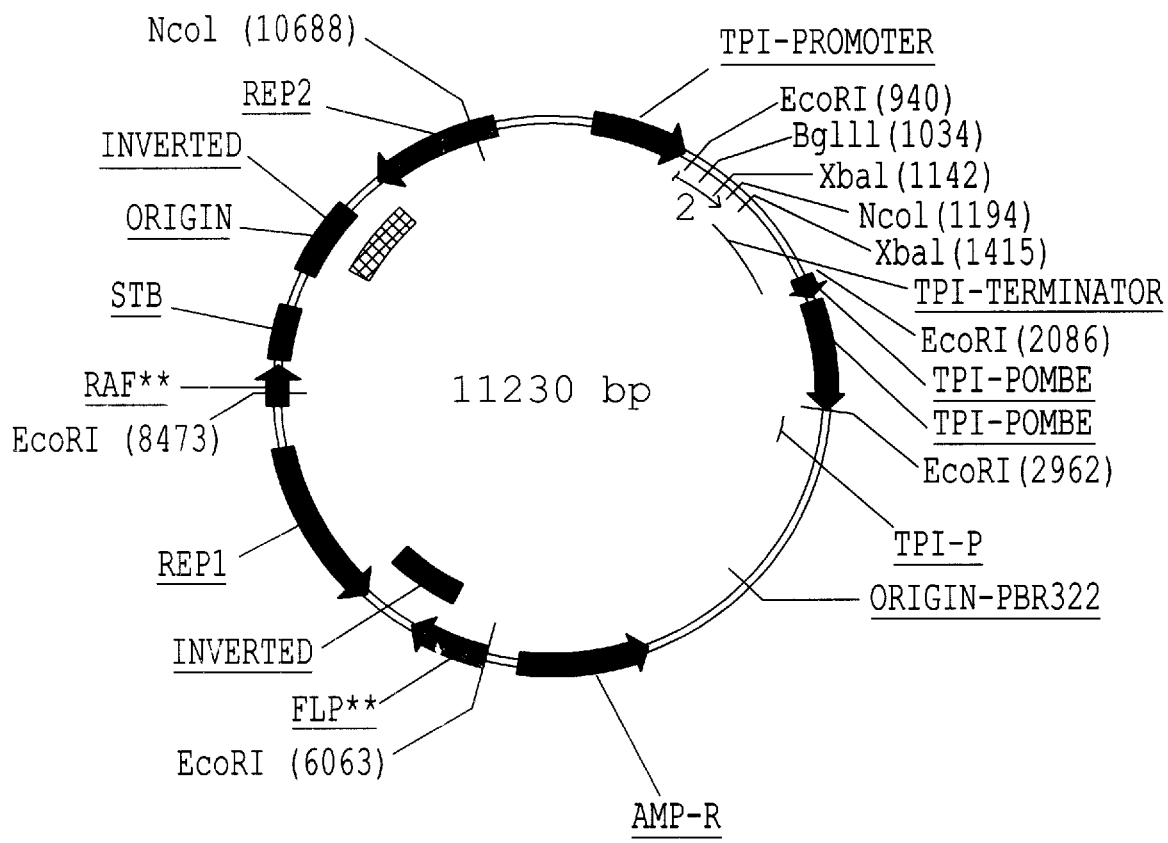
FIG. 20 shows the expression plasmid pAK721 containing genes expressing the N-terminally extended polypeptides of the invention. The symbols are as described in the legend of FIG. 13, with the exception that 2: Denotes the region encoding a signal/leader peptide (e.g. from the YAP3 signal peptide and LA19 leader peptide in conjunction with the Glu Glu Ala Glu Pro Lys N-terminally extended MI3 insulin precursor.

The plasmid pAK721 (FIG. 20) was cut with the restriction endonucleases BglII and XbaI and the vector fragment of 10849 nucleotides isolated. The plasmid pAK721 was cut with the restriction endonucleases BglII and NcoI and the DNA fragment of 160 nucleotides isolated. The three DNA fragments was ligated and transformed into a competent *E. coli* strain (R−, M+) followed by selection with ampicillin resistance.

Plasmid from the resulting *E. coli* was isolated and shown to contain the correct DNA sequence for the Glu Glu Gly Glu Pro Lys-MI3 insulin precursor DNA and to be inserted after the DNA encoding the synthetic LA19 leader DNA. The plasmid was named pAK773.

The DNA sequence encoding the YAP3 signal peptide-LA19 leader Glu Glu Gly Glu Pro Lys-MI3 insulin precursor complex are shown in FIG. 21.

The plasmid pAK773 was transformed into *S. cerevisiae* strain MT663 as described in PCT/DK95/00250 and the resulting strain was named yAK773.

The yeast expression plasmid pAK773 is of the C-POT type and is similar to those described in WO EP 171 142, which contain the *Schizosaccharomyces pombe* triose phosphate isomerase gene (POT) for plasmid selection and stabilisation in *S. cerevisiae*. pAK773 also contain the *S. cerevisiae* triose phosphate isomerase promoter and terminator. The promoter and terminator are similar to those described in the plasmid pKFN1003 (described in WO 90/100075) as are all sequences in plasmid except the sequence between the EcoRIXbaI fragment encoding the YAP3 signal peptide-LA19 leader peptide-Glu Glu Gly Glu Pro Lys-MI3 insulin precursor.

We claim:

1. A DNA construct encoding a precursor polypeptide having the following structure;

signal peptide-leader peptide-$X^1$-$X^2$-$X^3$-$X^4$-$X^5$-$X^6$-$X^7$-heterologous protein wherein $X^1$ is Lys or Arg;

$X^2$ is Lys or Arg, $X^1$ and $X^2$ together defining a yeast processing site;

$X^3$ is Glu or Asp;

$X^4$ is Glu or Asp;

$X^5$ is a peptide bond or is 1–9 amino acids which may be the same or different;

$X^6$ is Pro; and $X^7$ is Lys or Arg, and wherein expression of said DNA construct in yeast results in secretion of a polypeptide having the structure $X^3$-$X^4$-$X^5$-$X^6$-$X^7$-heterologous protein.

2. A DNA construct encoding a precursor polypeptide having the following structure:

signal peptide-leader peptide-$X^1$-$X^2$-$X^3$-$X^4$-$X^5$-$X^6$-$X^7$-heterologous protein wherein $X^1$ is Lys or Arg;

$X^2$ is Lys or Arg, $X^1$ and $X^2$ together defining a yeast processing site;

$X^3$ is Glu or Asp;

$X^4$ is Glu or Asp;

$X^5$ is a peptide bond or 1–9 amino acid residues selected from the group of Glu, Ala, Pro, Lys, Arg, Leu, Ile, Gly, and Thr;

$X^6$ is Pro; and $X^7$ is Lys or Arg, and wherein expression of said DNA construct in yeast results in secretion of a polypeptide having the structure $X^3$-$X^4$-$X^5$-$X^6$-$X^7$-heterologous protein.

3. A DNA construct encoding a precursor polypeptide having the following structure:

signal peptide-leader peptide-$X^1$-$X^2$-Y-heterologous protein wherein $X^1$ is Lys or Arg; $X^2$ is Lys or Arg; $X^1$ and $X^2$ together define a yeast processing site; and Y is Glu Glu Ala Glu Ala Glu Xaa Xaa Xaa Arg Ala Pro Arg (SEQ ID NO:94).

4. A DNA construct encoding a polypeptide having the following structure:

signal peptide-leader peptide-$X^1$-$X^2$-Y-heterologous protein wherein $X^1$ is Lys or Arg; $X^2$ is Lys or Arg; $X^1$ and $X^2$ together define a yeast processing site; and Y is Glu Glu Ala Glu Ala Glu Ala Glu Pro Arg (SEQ ID NO:44).

5. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Ala Glu Ala Glu Ala Glu Pro Lys (SEQ ID NO:45).

6. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Ala Glu Ala Glu Ala Pro Lys (SEQ ID NO:72).

7. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Ala Glu Ala Pro Lys (SEQ ID NO:51).

8. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Ala Pro Lys (SEQ ID NO:52).

9. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Glu Glu Pro Lys (SEQ ID NO:54).

10. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Glu Pro Lys (SEQ ID NO:55).

11. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Pro Lys (SEQ ID NO:57).

12. A DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Ala Glu Pro Lys (SEQ ID NO:1).

13. DNA construct encoding a polypeptide having the following structure:

signal peptide-leader peptide-X$^1$-X$^2$-Y-heterologous protein wherein X$^1$ is Lys or Arg; X$^2$ is Lys or Arg; X$^1$ and X$^2$ together define a yeast processing site; and Y is Glu Glu Gly Glu Pro Lys (SEQ ID NO:2).

14. A process for producing a heterologous protein, said process comprising;

(i) cultivating a yeast cell comprising a DNA construct, wherein said DNA construct encodes a precursor polypeptide having the following structure:

signal peptide-leader peptide-X$^1$-X$^2$-X$^3$-X$^4$-X$^5$-X$^6$-X$^7$-heterologous protein wherein
X$^1$ is Lys or Arg,
X$^2$ is Lys or Arg, X$^1$ and x$^2$ together defining a yeast processing site;
X$^3$ is Glu or Asp;
X$^4$ is Glu or Asp:
X$^5$ is a peptide bond or is 1–9 amino acids which may be the same or different;
X$^6$ is Pro; and
X$^7$ is Lys or Arg.
and wherein said cultivating is in a suitable medium to obtain expression and secretion of the X$^3$-X$^4$-X$^5$-X$^6$-X$^7$ N-terminally extended heterologous protein;
(ii) isolating the expressed protein from the culture medium, and
(iii) removing the X$^3$-X$^4$-X$^5$-X$^6$-X$^7$ sequence from the protein by proteolytic cleavage in vitro with a proteolytic enzyme specific for a basic amino acid residue.

15. The process of claim 14, wherein the proteolytic enzyme is selected from the group consisting of trypsin, *Achromobacter lyticus* protease I, Enterokinase, *Fusarium oxysporum* trypsin-like protease, and YAP3.

16. The DNA construct of claim 1, wherein the leader peptide is selected from the group consisting of SEQ ID NOs:31–41.

17. The DNA construct of claim 12, wherein the leader peptide is selected from the group consisting of SEQ ID NOs:31–41.

18. The DNA construct of claim 13, wherein the leader peptide is selected from the group consisting of SEQ ID NOs:31–41.

19. A DNA construct encoding a polypeptide having the following structure:

signal peptide-leader peptide-X$^1$-X$^2$-Y-heterologous protein wherein the leader peptide is SEQ ID NO:31, X$^1$ is Lys or Arg, X$^2$ is Lys or Arg, and X$^1$ and X$^2$ together define a yeast processing site, and Y is SEQ ID NO:1.

20. The process of claim 14, wherein X$^3$ and X$^4$ are each Glu.

21. The process of claim 14, wherein the signal peptide is α-factor signal peptide, yeast aspartic protease 3 signal peptide, mouse salivary amylase signal peptide, carboxypeptidase signal peptide, or yeast BAR1 signal peptide.

22. The process of claim 21, wherein the signal peptide is α-factor signal peptide.

23. The process of claim 14, wherein tie leader peptide is a natural leader or a synthetic leader peptide.

24. The process of claim 23, wherein the leader peptide is a synthetic leader selected from the group consisting of SEQ ID Nos: 31–41.

25. The process of claim 14, wherein the heterologous protein is selected from the group consisting of aprotinin, tissue factor pathway inhibitor or other protease inhibitors, insulin-like growth factor I or II, human or bovine growth hormone, interleukin, tissue plasminogen activator, glucagon, gliucagon-like peptide-1, Factor VII, Factor VIII, Factor XIII, platelet-derived growth factor, enzymes, insulin or an insulin precursor, and a functional analogue of any of the foregoing.

26. The process of claim 25, wherein the heterologous protein is insulin or an insulin precursor or a functional analogue thereof.

27. A process for producing a heterologous protein, comprising:
(i) cultivating a yeast cell comprising a DNA construct, wherein said DNA construct encodes a precursor polypeptide having the following structure:

signal peptide-leader peptide-$X^1$-$X^2$-$X^3$-$X^4$-$X^5$-$X^6$-$X^7$-heterologous protein wherein
$X^1$ is Lys or Arg;
$X^2$ is Lys or Arg, $X^1$ and $X^2$ together defining a yeast processing site;
$X^3$ is Glu or Asp;
$X^4$ is Glu or Asp;
$X^5$ is a peptide bond or 1–9 amino acid residues selected from the group of Glu, Ala, Pro, Lys, Arg, Leu, Ile, Gly, and Thr;
$X^6$ is Pro; and
$X^7$ is lys or Arg,
and wherein said cultivating is in a suitable medium to obtain expression and secretion of the $X^3$-$X^4$-$X^5$-$X^6$-$X^7$ N-terminally extended heterologous protein,
(ii) isolating the expressed protein from the culture medium, and
(iii) removing the $X^3$-$X^4$-$X^5$-$X^6$-$X^7$ sequence from the protein by proteolytic cleavage in vitro with a proteolytic enzyme specific for a basic amino acid residue.

28. The process of claim 27, wherein $X^3$ and $X^4$ are each Glu.

29. The process of claim 27, wherein the signal peptide is α-factor signal peptide, yeast aspartic protease 3 signal peptide, mouse salivary amylase signal peptide, carboxypeptidase signal peptide, or yeast BAR1 signal peptide.

30. The process of claim 29, wherein the signal peptide is α-factor signal peptide.

31. The process of claim 27, wherein the leader peptide is a natural leader or a synthetic leader peptide.

32. The process of claim 31, wherein the leader peptide is a synthetic leader selected from the group consisting of SEQ ID Nos: 31–41.

33. The process of claim 27, wherein the heterologous protein is selected from the group consisting of aprotinin, tissue factor pathway inhibitor or other protease inhibitors, insulin-like growth factor I or II, human or bovine growth hormone, interleukin, tissue plasminogen activator, glucagon, glucagon-like peptide-1, Factor VII, Factor VIII, Factor XIII, platelet-derived growth factor, enzymes, insulin or an insulin precursor, and a functional analogue of any of the foregoing.

34. The process of claim 33, wherein the heterologous protein is insulin or an insulin precursor or a functional analogue thereof.

35. The process of claim 27, wherein the proteolytic enzyme is selected from the group consisting of trypsin, *Achromobacter lyticus* protease I, Enterokinase, *Fusarium oxysporum* trypsin-like protease, and YAP3.

* * * * *